(12) United States Patent
Andersen et al.

(10) Patent No.: US 6,505,654 B1
(45) Date of Patent: Jan. 14, 2003

(54) MEDICAL STENTS FOR BODY LUMENS EXHIBITING PERISTALTIC MOTION

(75) Inventors: Erik Andersen, Roskilde (DK); Ernst Peter Strecker, Karlsruhe (DE)

(73) Assignee: Scimed Life Systems, Inc., Maple Grove, MN (US)

( * ) Notice: Subject to any disclaimer, the term of this patent is extended or adjusted under 35 U.S.C. 154(b) by 167 days.

(21) Appl. No.: 09/577,540

(22) Filed: Oct. 20, 2000

Related U.S. Application Data

(62) Division of application No. 08/922,156, filed on Sep. 2, 1997, now Pat. No. 6,146,416, which is a continuation of application No. 08/528,061, filed on Sep. 14, 1995, now Pat. No. 5,662,713, which is a continuation of application No. 07/960,584, filed on Oct. 13, 1992, now abandoned, which is a continuation of application No. 07/773,847, filed on Oct. 9, 1991, now Pat. No. 5,234,457.

(51) Int. Cl.[7] ............................... B21F 45/00
(52) U.S. Cl. ..................... 140/107; 140/71 R
(58) Field of Search ............... 140/71 R, 107; 242/448

(56) References Cited

U.S. PATENT DOCUMENTS 2,565,846 A * 8/1951 Goodloe .................. 140/107
4,124,183 A * 11/1978 Herrig et al. ............. 140/107

(List continued on next page.)

FOREIGN PATENT DOCUMENTS

| DE | 24/61370 | 3/1975 |
|----|----------|--------|
| DE | 3640745 | 11/1986 |
| DE | 3918736 A1 | 12/1990 |
| EP | 0 481 365 A1 | 4/1992 |
| EP | 10 492 481 A1 | 7/1992 |
| GB | 1205743 | 9/1970 |
| WO | 82/01647 | 5/1982 |
| WO | 83/03752 | 11/1983 |
| WO | 84/02266 | 6/1984 |
| WO | WO 87/704935 | 8/1987 |
| WO | WO 92/06638 | 4/1992 |
| WO | WO 93/06781 | 4/1993 |

OTHER PUBLICATIONS

EP Search 93 92 3362 dated Apr. 26, 1996.

(List continued on next page.)

*Primary Examiner*—Lowell A. Larson
(74) *Attorney, Agent, or Firm*—Kriegsman & Kriegsman

(57) ABSTRACT

A stent for reinforcement of the lumen of a peristaltic organ is formed by knitting preferably a nitinol wire into a pattern of overlapping loops selected such that from a relaxed state each row of loops may shift axially relative to and independently of the rows on either side. This local lengthening and shortening accommodate peristalsis of the organ without migrating within the organ. A stent is also shown which comprises two resilient cylindrical mesh layers and a semipermeable compliant membrane such as expanded polytetrafluoroethylene, sandwiched between. The two mesh layers may be knit of a flexible filament, and the knit may be configured so that the stent can adapt to peristalsis of the body lumen. A method is also shown of manufacturing a delivery system for a resilient tubular device such as a stent so that the device can be inserted into the body in a substantially reduced diameter. The method uses a confining block having a bore and a slot leading into the bore. The tubular device is pinched and inserted into the bore and the slot, two mandrels are inserted into the bore, one inside the device and one outside and the mandrels are revolved about each other to roll the device on itself.

6 Claims, 17 Drawing Sheets-

U.S. PATENT DOCUMENTS

| | | | |
|---|---|---|---|
| 4,576,142 A | 3/1986 | Schiff | |
| 4,681,092 A | 7/1987 | Cho et al. | |
| 4,705,517 A | 11/1987 | DiPisa, Jr. | |
| 4,733,665 A | 3/1988 | Palmaz | |
| 4,800,882 A | 1/1989 | Gianturco | |
| 4,856,516 A | 8/1989 | Hillstead | |
| 4,872,874 A | 10/1989 | Taheri | |
| 4,950,227 A | 8/1990 | Savin et al. | |
| 5,015,253 A | 5/1991 | MacGregor | |
| 5,035,706 A | 7/1991 | Giantureo et al. | |
| 5,064,435 A | 11/1991 | Porter | |
| 5,197,978 A | 3/1993 | Hess | |
| 5,226,913 A * | 7/1993 | Pinchuk | 140/71 R |
| 5,246,445 A | 9/1993 | Yachia et al. | |
| 5,354,309 A | 10/1994 | Schnepp-Pesch et al. | |

OTHER PUBLICATIONS

Microvasive Boston Scientific Corporation Ultraflex Esophageal Prosthesis Literature, "Setting New Standards for Management of Esophageal Obstruction," May, 1992.

Boston Scientific Corporation Strecker Esophageal Stent Literature, New Product Bulletin, Apr. 1992.

Duprat, Gerard, Jr., et al. "Flexible Balloon–expanded Stents for Small Vessels," *Radiology*, Scientific Assembly & Annual Meeting Scientific Program. 1996 vol. 161.

Strecker, E.P., et al. "A New Vascular Balloon–expandable Prosthesis—Experimental Studies and Fist Clinical Results," *Journal of Interventional Radiology*, 1987, pp. 59–62.

Strecker, E.P., et al. "Expandable Tubular Stents for Treatment of Arterial Occlusive Diseases: Experimental and Clinical Results", *Radiology*, vol. 175. No. 1, pp. 97–102, Apr. 1990.

L.A. Loizou et al., Gastrointestinal Endoscopy, Mar./Apr. 1992, vol. 38, No. 2, pp. 158–164.

Schaer et al., Gastrointestinal Endoscopy. Jan./Feb. 1992. vol. 38, No. 1, pp. 7–11.

Rosch et al., Radiology. Feb. 87, vol. 162. pp. 481–485.

Lawrence J. Mills, M.D., et al., "Avoidance of Esophageal Stricture Following Severe Caustic Burns by the Use of an Intraluminal Stent," *The Annals of Thoracic Surgery*, vol. 28, No. 1. Jul. 1979.

Roubin, G.S., et al. "Early and late results of intracoronoary arterial stenting after coronary angioplasty in dogs," *Circulation*, vol. 76 No. 4. pp. 891–897, 1987.

Duprat Gerard Jr., et al., "Flesivle Ballon–expanded Stent for Small Vessels," *Radiology*, vol. 162, No. 1, pp. 276–278, 1987.

* cited by examiner

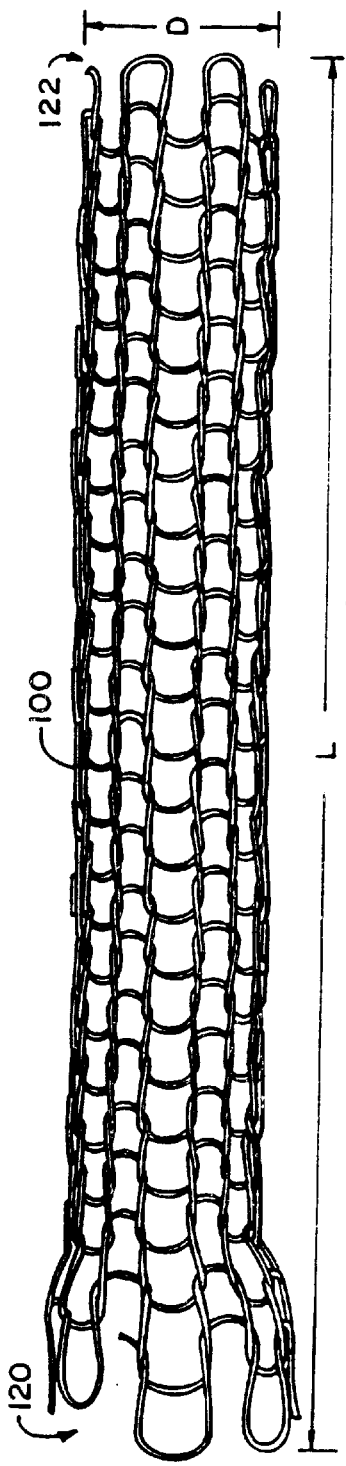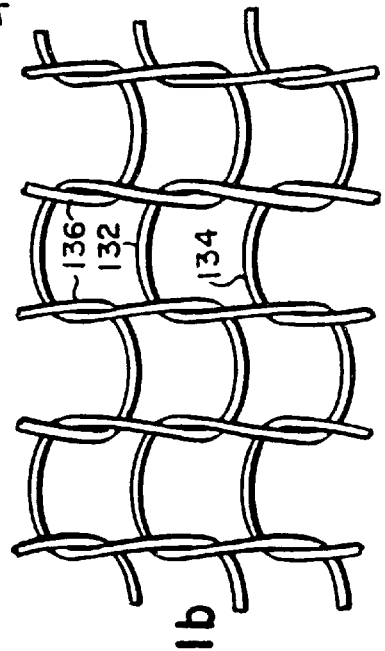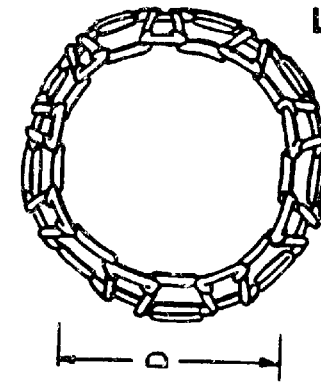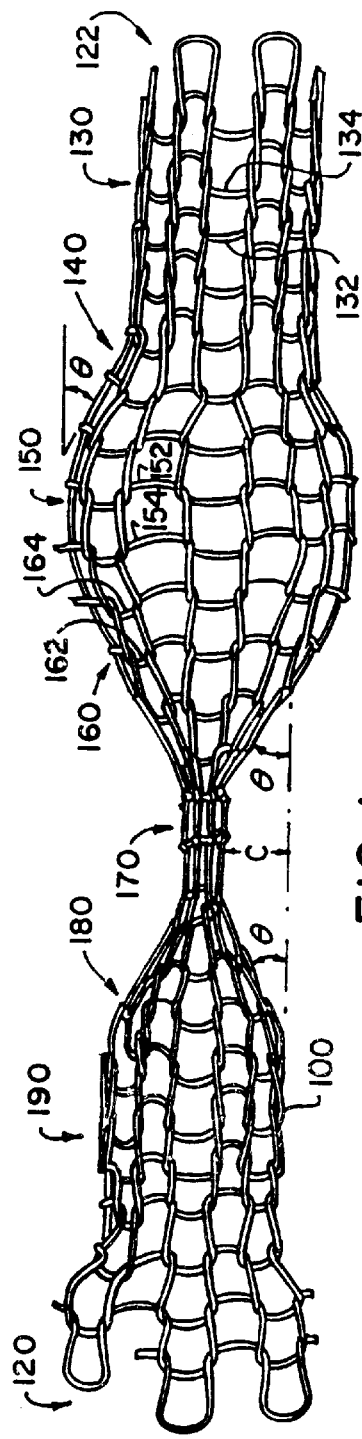
FIG. 1
FIG. 1a
FIG. 1b
FIG. 1c

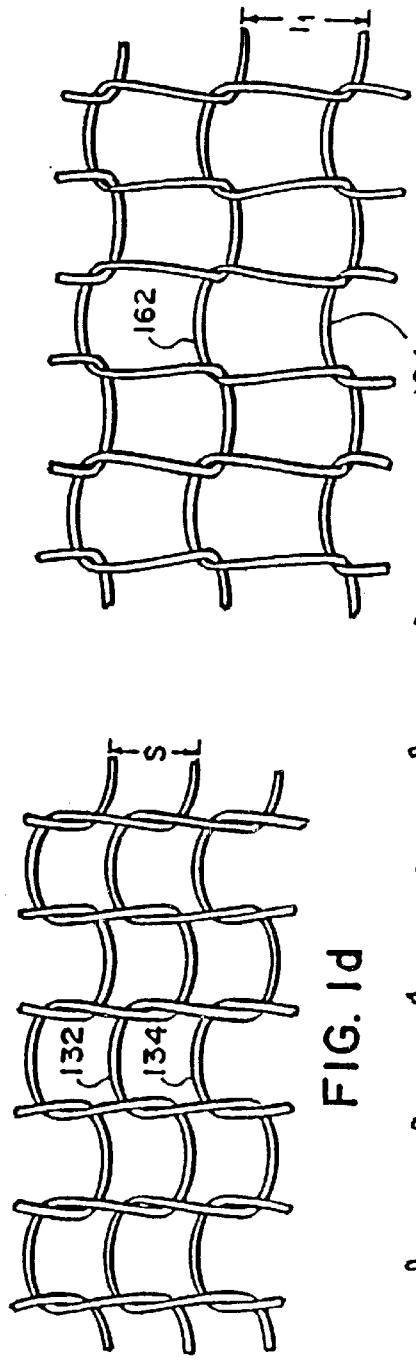
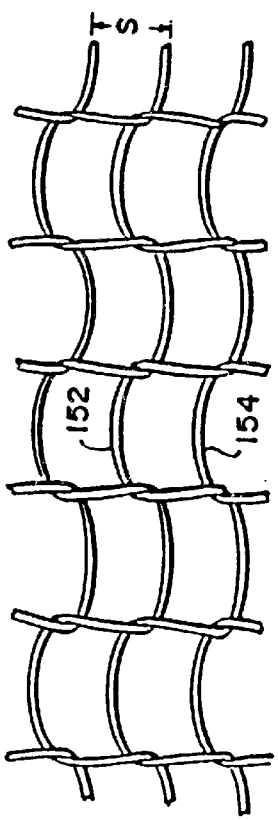
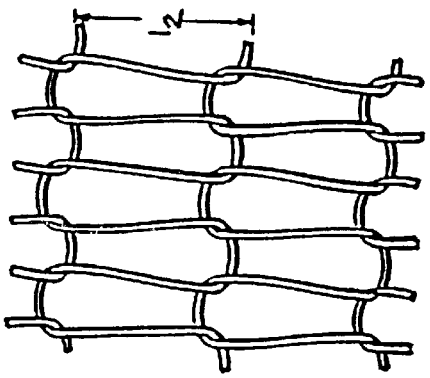
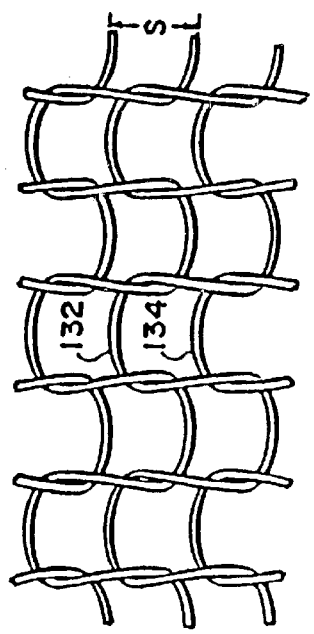
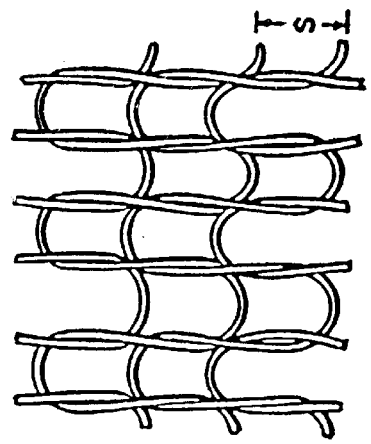

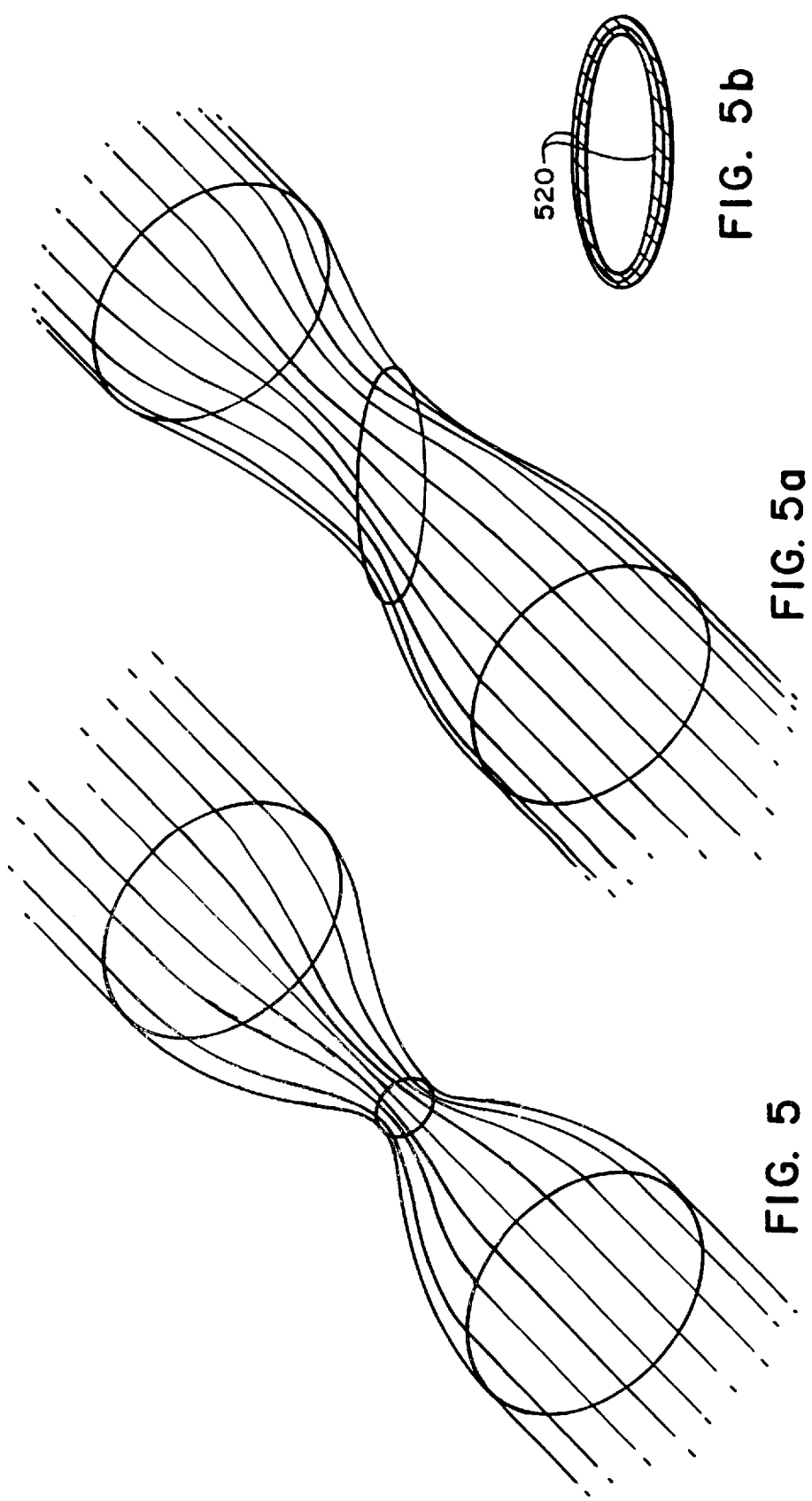

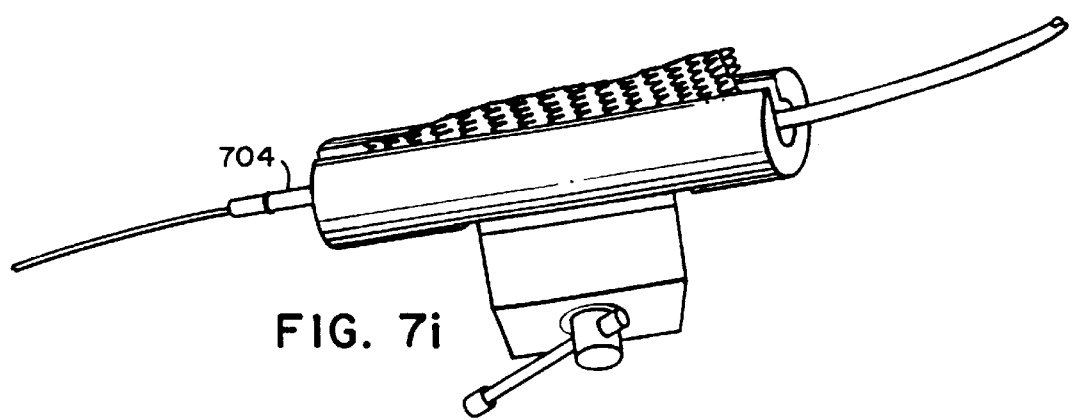
FIG. 7i
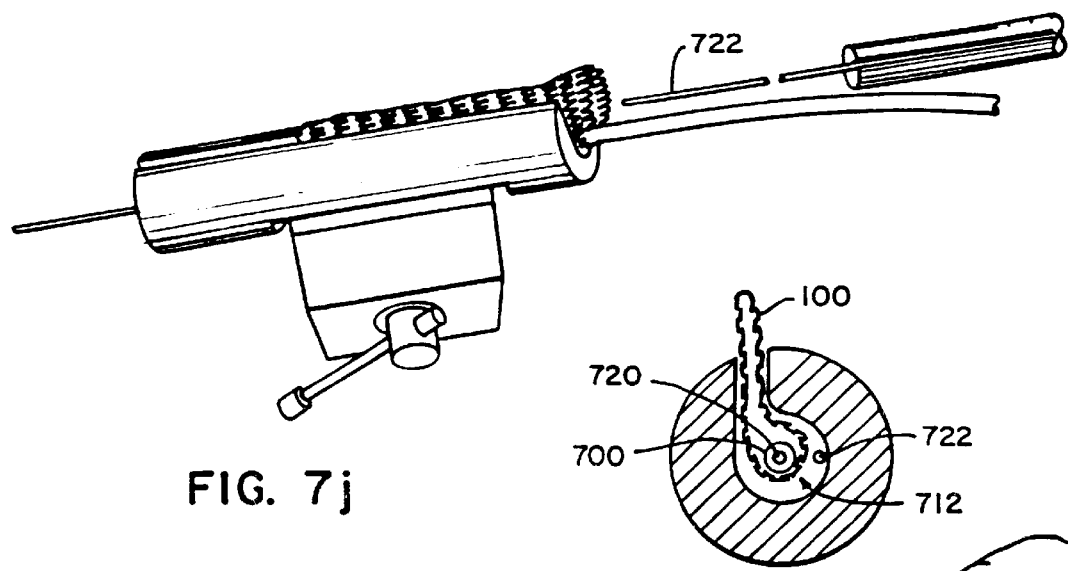
FIG. 7j
FIG. 7k
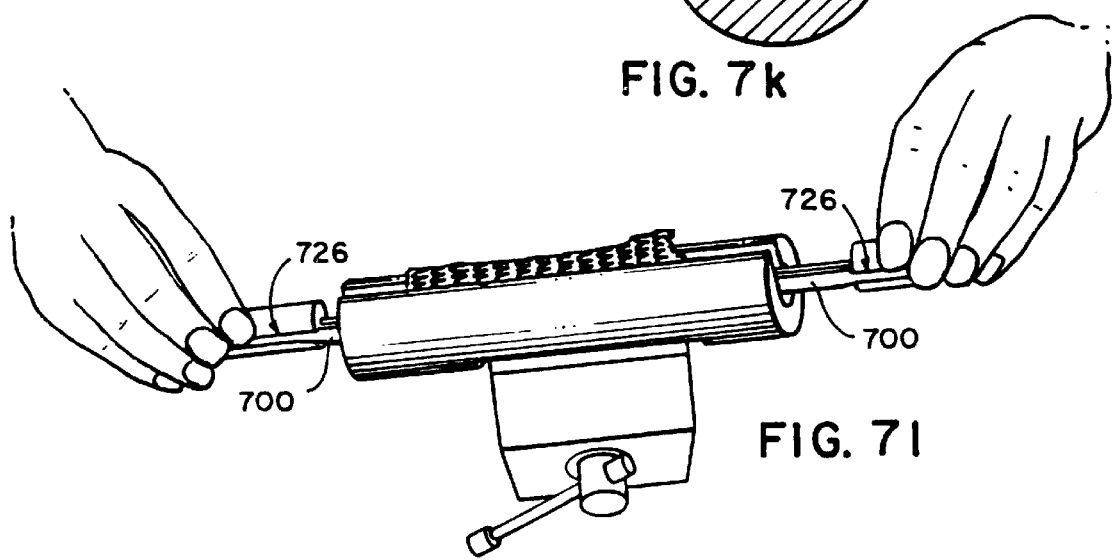
FIG. 7l

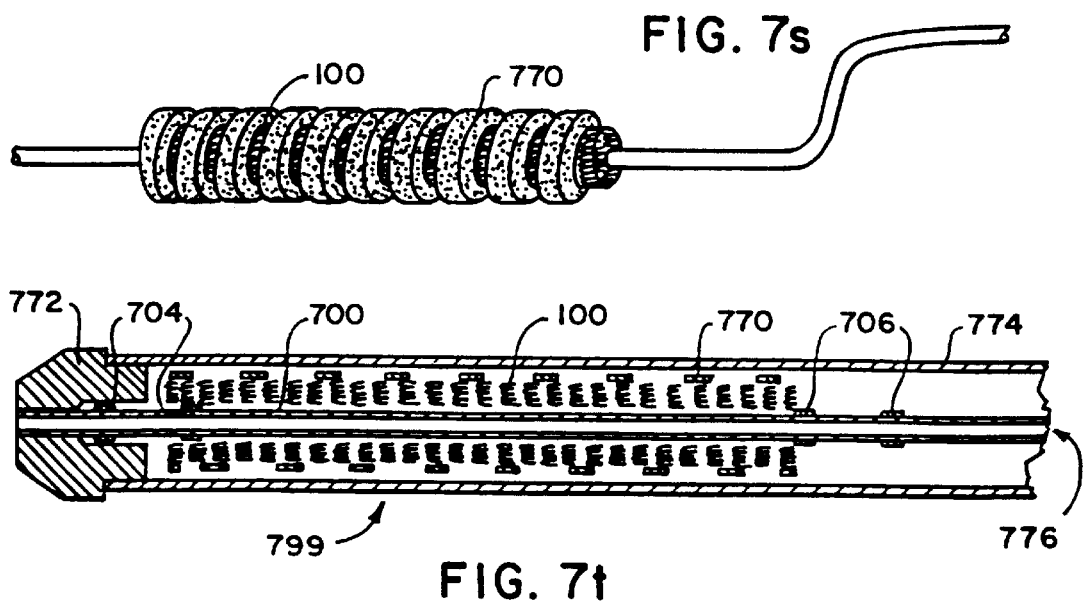
FIG. 7s
FIG. 7t
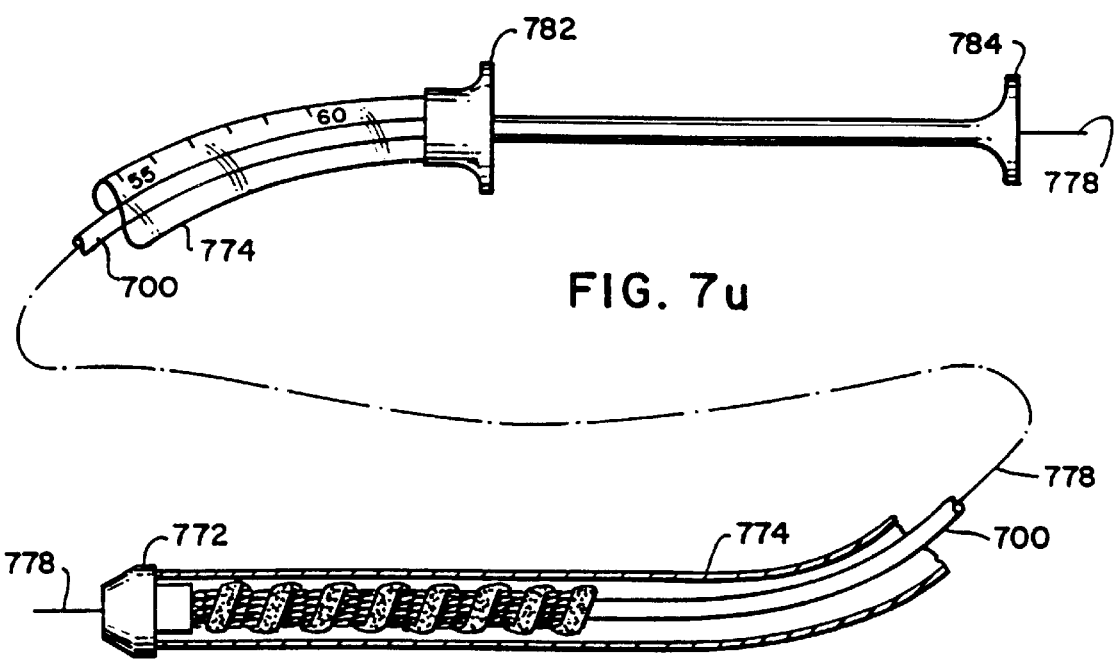
FIG. 7u

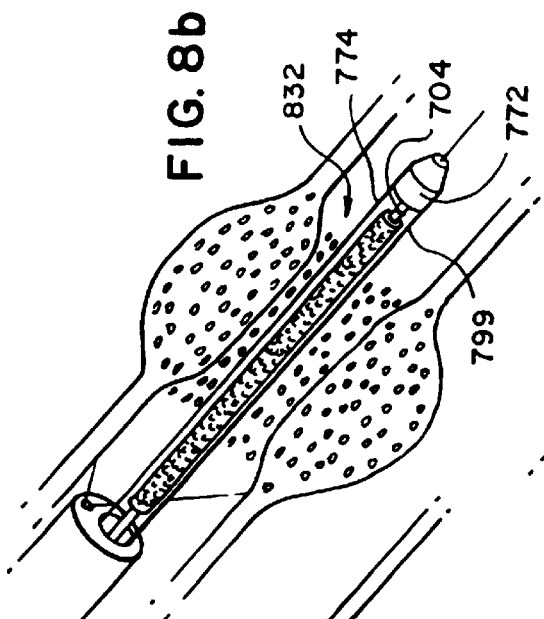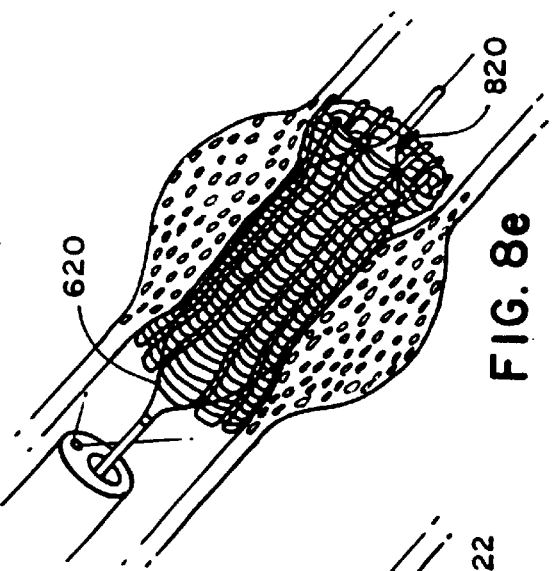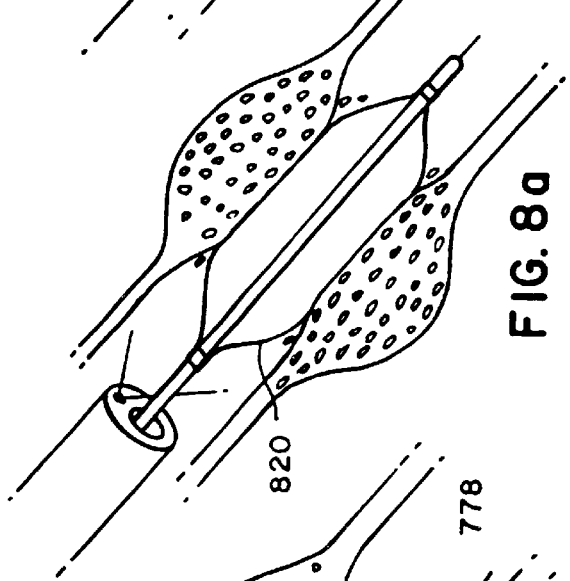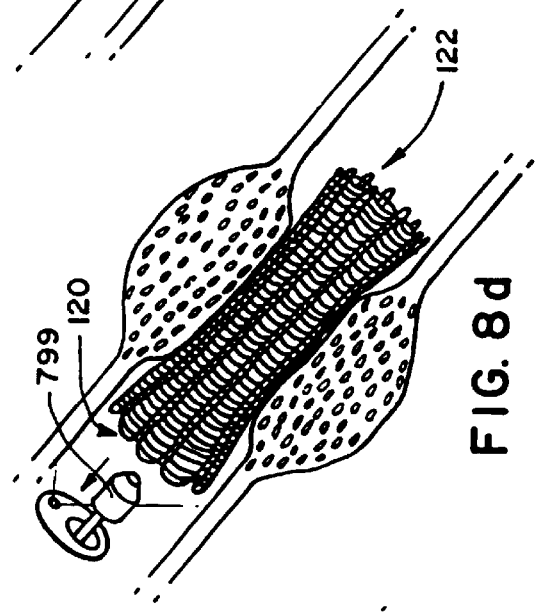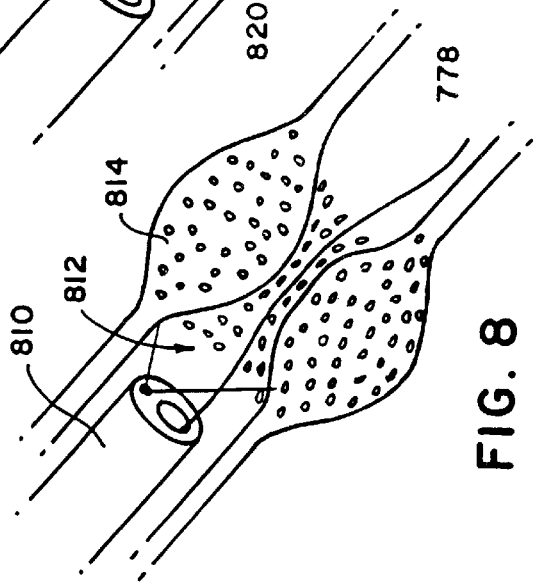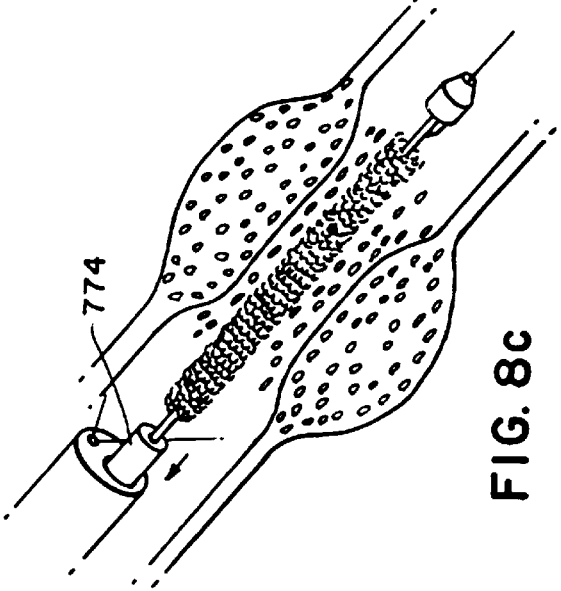

MEDICAL STENTS FOR BODY LUMENS EXHIBITING PERISTALTIC MOTION

CROSS REFERENCE TO RELATED APPLICATIONS

This application is a divisional of application Ser. No. 08/922,156, filed Sep. 2, 1997, now U.S. Pat No. 6,146,416, which is a continuation of application Ser. No. 08/528,061, filed Sep. 14, 1995, now U.S. Pat. No. 5,662,713, which is a continuation of application Ser. No. 07/960,584, filed Oct. 13, 1992, now abandoned, which is a continuation of application Ser. No. 07/773,847, filed Oct. 9, 1991, now U.S. Pat. No. 5,234,457.

FIELD OF THE INVENTION

This invention relates to endoprosthetic stents that are placed within body lumens that exhibit physiologic motion such as peristaltic motion.

BACKGROUND OF THE INVENTION

Medical stents are tubular endoprostheses placed within the body to perform a function such as maintaining open a body lumen, for example, a passageway occluded by a tumor. Typically, the stent is delivered inside the body by a catheter that supports the stent in a compacted form as it is transported to the desired site. Upon reaching the site, the stent is expanded so that it engages the walls of the lumen. The expansion mechanism may involve forcing the stent to expand radially outward, for example, by inflation of a balloon carried by the catheter, to inelastically deform the stent and fix it at a predetermined expanded position in contact with the lumen wall. The expansion balloon can then be deflated and the catheter removed.

In another technique, the stent is formed of a highly elastic material that will self-expand after being compacted. During introduction into the body, the stent is restrained in the compacted condition. When the stent has been delivered to the desired site for implantation, the restraint is removed, allowing the stent to self-expand by its own internal elastic restoring force.

Strictures of the esophagus often produce obstructive dysphagia resulting in debilitating malnutrition. To date, the theoretical advantages of placing a plastic stent to restore the patient's ability to swallow have been offset by technical difficulty of placement, morbidity and mortality associated with the procedure, and poor long-term prosthesis performance. In particular, previous stents have transmitted the force and deformation of peristaltic waves inappropriately, for instance causing the stent to creep toward the stomach, perforate the esophagus, or rupture the aorta.

SUMMARY OF THE INVENTION

In a first aspect, the invention features a method for providing reinforcement to the lumen of a peristaltic organ. The stent is formed by knitting a filament into interknit loops, the pattern of the loops selected such that from a relaxed state each row of loops may shift axially relative to and independently of the rows on either side. The local lengthening and shortening allowed by the shifting allows the stent to accommodate the peristalsis of the organ without migrating within the organ.

Preferred embodiments of the stent feature the following. The lumen treated is the esophagus. The elongation factor $\epsilon$ by which the stent can locally lengthen by shifting is related to the angle $\theta$ at which the lumen can incline inward by the relationship: $\epsilon=1.0/\cos\theta$. The stent is knitted of metal wire to be self-expandable such that the stent expands outward against the body lumen wall by an elastic restoring force of the wire. The stent is knitted from nitinol wire having a diameter of about 0.15 mm. The stent, in its free state, has a point of constricted cross-section. The constriction may have a valve.

A stent according to the invention offers the following advantages. The stent exerts a constant, gentle radial force on the wall of the lumen that maintains lumen patency and actively resists compression, as by a tumor. The inherent flexibility of the knitted stent adapts to peristalsis, transmitting the peristaltic wave to the lumen, but without changing overall length or creeping. This reduces complications and promotes long-term stability, patency, and patient comfort. The force exerted by the stent against the lumen is sufficient to compress the capillaries of the organ so that growth into the lumen is retarded. The stent can be delivered via a low-profile delivery system which is smaller than a standard endoscope. The small diameter of the delivery system simplifies implantation by eliminating the need for pre-dilating the stricture, and allows placement even in patients with tortuous esophageal anatomy or strictures prone to perforation by plastic stents.

In a second aspect, the invention features a stent for providing reinforcement to a selected region of a selected body lumen. The stent comprises two resilient cylindrical mesh layers and a semi-permeable compliant membrane sandwiched between.

Preferred embodiments of the invention feature the following. The two mesh layers may be knit of a flexible filament, and the knit may be configured so that the stent can adapt to peristalsis of the body lumen. The membrane is composed of expanded polytetrafluoroethylene.

The invention or preferred embodiments thereof may feature the following advantages. The semi-permeable membrane prevents cell ingrowth of the stent. The force exerted by the stent against the lumen is sufficient to compress the capillaries of the organ so that growth into the lumen is retarded.

In a third aspect, the invention features a method of manufacturing a delivery system for a resilient tubular device so that the tubular device can be inserted into the body in a substantially reduced diameter. The method uses a confining block having a bore and a slot leading into the bore. The tubular device is pinched and inserted into the bore and the slot. Two mandrels are inserted into the bore, one inside the tubular device and one outside. The mandrels are revolved about each other to roll the tubular device on itself until the tubular device is entirely rolled and confined at the reduced diameter within the bore. The tubular device is removed from the bore while being restrained in the reduced diameter.

Preferred embodiments of the method of manufacture feature the following. The removing step may be accomplished by pushing the tubular device from the end of the bore and restraining the tubular device as it emerges. The restraining my be by means of wrapping a wire around the tubular device. The slot may be tangent to the bore of the confining block. The tubular device may be a stent knit of an elastic filament. One of the mandrels may be part of the delivery system that will be used to deliver the stent.

The inventive method of manufacturing the stent features the following advantages. Certain prior methods required several operators to simultaneously hold and constrain the resiliency of the stent and hurt the fingers of the operators.

The method of the invention requires only one operator and is comfortable to execute. The stent delivery systems produced by the method are more uniform than those manufactured by previous methods, both in distribution of stresses within a single stent and in variation between stents, thus avoiding deformation of the stent during manufacture and allowing the physician to place the stent more precisely in the patient. A stent delivery system manufactured according to the method has a small profile, and thus minimizes trauma to the patient during implantation.

Other advantages and features of the invention will become apparent from the following description of a preferred embodiment, and from the claims.

BRIEF DESCRIPTION OF THE DRAWINGS

FIGS. 1 and 1c are perspective views of a stent according to the invention.

FIG. 1a is an end elevation view of the stent.

FIGS. 1b, 1d–1h, 4a, and 6 are detail views of the knitted loops of a knitted stent.

FIGS. 5, 5a, and 5b are schematic representations of alternate embodiments of the stent.

FIGS. 6a, 7, 7a, 7c–7j, 7l, 7m, and 7p–s are perspective views of tools and a time sequence of steps in a process for manufacturing a delivery system for the stent.

FIGS. 7b, 7k, 7n, and 7o are cross-sectional views taken during the process of manufacturing the delivery system.

FIG. 7t is a sectional view of the delivery system.

FIG. 7u is a perspective view of the delivery system, cut away.

FIGS. 8 and 8a–8e are a time sequence of sectional views of an esophagus showing delivery of a stent.

DESCRIPTION OF PREFERRED EMBODIMENTS

Figure 2A:
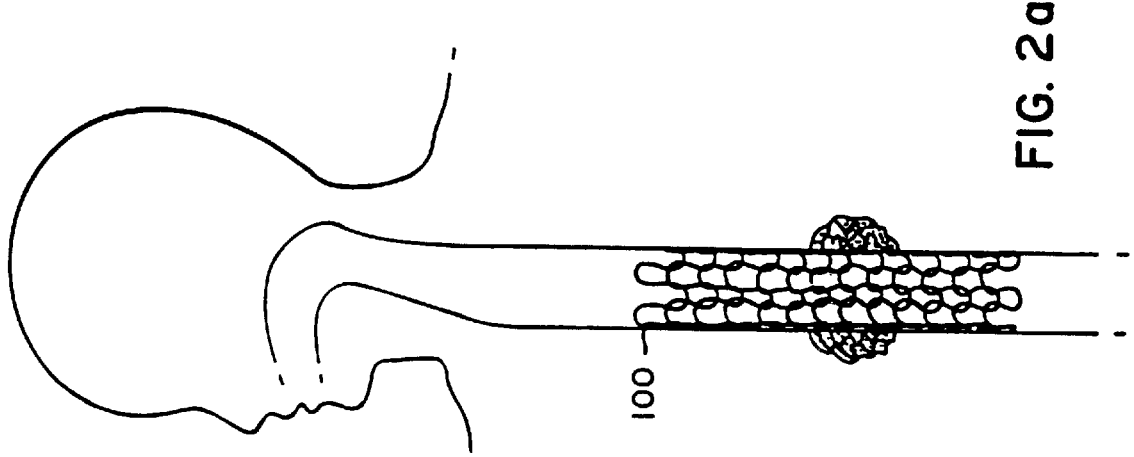
FIGS. 2, 2a, 3, and 3a–3e are sectional views of a body, showing effects and operation of a stent in the esophagus.

Referring to FIGS. 1 and 1a, a stent 100 according to a preferred embodiment is formed of a knit cylinder with length L and diameter D. The knitting forms a series of loosely-interlocked knitted loops (e.g., as indicated by adjacent loops 132 and 134 in FIG. 1b) that may slide with respect to each other. This sliding or shifting allows the stent to adapt to the movement of the organ without moving axially in the organ. The adaptation is accomplished with mere bending of the stent filament.

The stent maintains its axial working length L when locally radially compressed, by locally lengthening or shortening due to shifting of the rows of loops relative to each other. FIG. 1c shows a region 130 of the stent not under radial compression where adjacent loops 132 and 134 are in an overlapping, relaxed configuration, and the heads of the loops are separated by a short distance s. In the case of an esophagus, a large piece of food distends the esophagus. At the first instant of the expansion, the wall may be deflected by an angle θ, but the diameter of the organ will not have changed appreciably. In such a region, 140 in FIG. 1c, the local length of the wall elongates by a factor 1/cos θ. The rows of loops of the stent shift axially with elastic deformation of the wire of the loops so that the separation of the heads increases to a loop length $l_1$, as shown in FIG. 1e. In the region of maximum expansion 150, the length of each portion of the esophagus returns to its rest length, but the diameter is extended. The knit loops of the stent can widen, as shown in FIG. 1f, to accommodate this extension. Returning again to considering any peristaltic organ, the organ contracts (c of FIG. 1c) to compress a region. In a region 160 where the wall is at an angle of deflection θ but the diameter is essentially equal to the rest diameter, the length of the wall of the organ will elongate by a factor 1/cos θ, and the loops will again pass through a state where their width is essentially the same as the rest width, but, by relative shifting of the rows of loops axially, they are extended to length $l_1$, the state shown in FIG. 1e. In a region of maximum compression 170, the wall of the organ is at its rest length, but the circumference is much reduced. In this region, the loops of the stent deform into the configuration of FIG. 1g, where the length of the loops is s but the width is compressed. Finally, as the peristalsis relaxes, the wall of the organ returns to its rest length and rest circumference, region 190 of FIG. 1c, and the loops of the stent return to the overlapped rest configuration of FIG. 1d.

In the case of organs that can constrict almost closed, as the lumen compresses radially the circumference shortens, and thus part of the length of the filament that contributes to the circumference of the stent in its rest state is freed to contribute to length, and thus the loops can lengthen to length $l_2$, as shown in FIG. 1h.

The lengthening from s to $l_2$ all occurs without significant elongation of the filament of the stent itself, only by elastic bending deformation and sliding of the rows of loops against one other. The ratio of the maximum local length to the relaxed local length, $l_2/s$, is determined by the configuration of the loops and the elastic limit of the material of the filament.

Referring again to FIG. 1c, the local lengthening in regions of radial extension, compression or slope does not substantially affect the loops in nearby regions that are not exposed to the radial compression, which are in turn free to elongate, contract or widen in response to the movements of their own local portions of the organ. Thus, the stent maintains its overall working length L even when locally extended or compressed. When the radial compression is released, the elasticity of the filament causes the stent to expand back to its original rest diameter D without change of the overall length, since adjacent loops in the region of compression slide back to the relaxed overlapped state, separated by distance s. Because the stent maintains point-for-point contact with the organ, averaged over a local area about the size of one loop, the stent maintains its placement in the organ, and does not migrate with the peristalsis.

A further property of the stent is that the state characterized by all adjacent loops being separated by distance s is the stable equilibrium between the elastic restoring forces of the wire and the compressive force of the esophagus. Thus, the stent automatically adjusts to overall length L regardless of the initial configuration of the loops and length of the stent. For example, if the loops are in extended positions as in FIG. 1e or 1h, then upon compression the loops adjacent the compressed region draw axially inward to the relaxed configuration in FIG. 1b, thus drawing the proximal end (120 of FIG. 1) and distal end 122 inward. When the compression releases, the loops in the region of the compression also shorten, since the ends 120 and 122 of the stent have been drawn inward and adjacent loops slide inward to adjust for the reduced overall length. Once the stent has settled into this equilibrium state, the overall length and position within the lumen are stable.

These features are enabled in the preferred stents of the invention by a sliding motion of adjacent filament loops, which in turn is enabled by the method of knitting that reduces overlap of the loops, as shown, and the elasticity of the filament and the shape of the loops. The sliding motion allows local axial lengthening or shortening of the stent substantially independently of other remotely located portions of the stent. The elasticity of the stent filament allows the stent and lumen to return to their desired patency when the compacting force is removed, without inelastic deformation. The loops are configured so that the stent assumes its desired diameter and overall length as the elastic restoring forces seek their minimum stress, the relaxed state of FIG. 1b. This minimization occurs when adjacent loops touch at their widest points, as for instance point 136 between loops 132 and 134.

Figure 2:
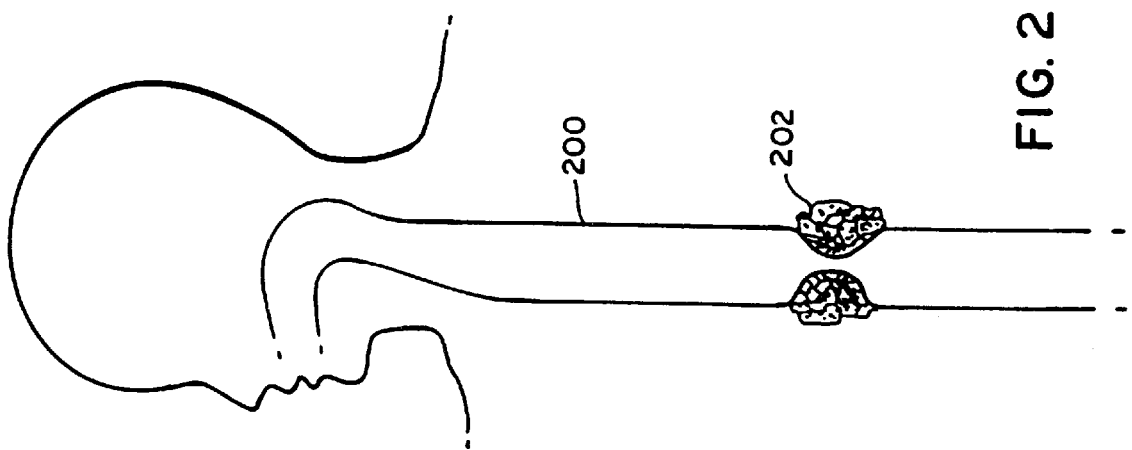

These features are particularly useful in body passages in which physiologic function includes motion of the lumen walls, such as peristaltic motion of the esophagus. For example, referring to FIG. 2, an esophagus 200 is occluded by a tumor 202. In FIG. 2a, after insertion of the stent 100, the lumen's patency is restored. Once implanted in the esophagus, the stent is held in a rest diameter that is slightly compressed by the esophagus from its free diameter when outside the body. It is the elastic restoring force of the stent resisting this compression that holds the stent in place.

Figure 3B:
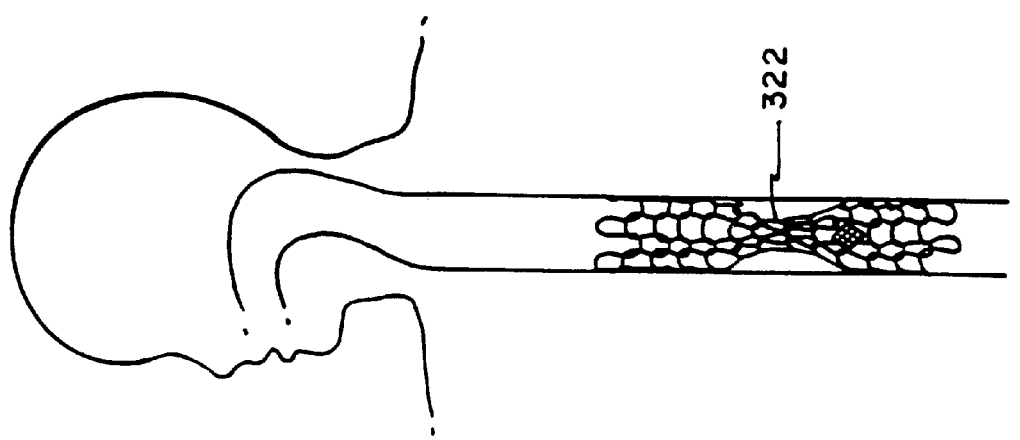
Figure 3A:
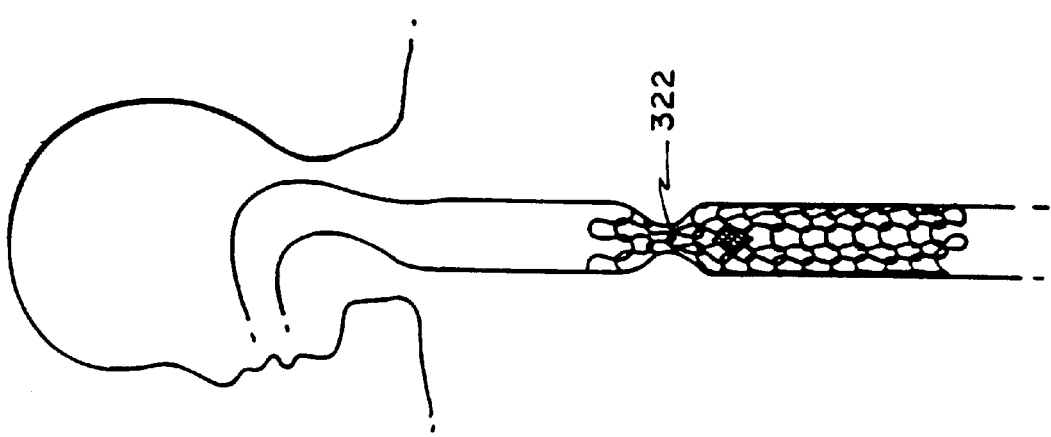
Figure 3:
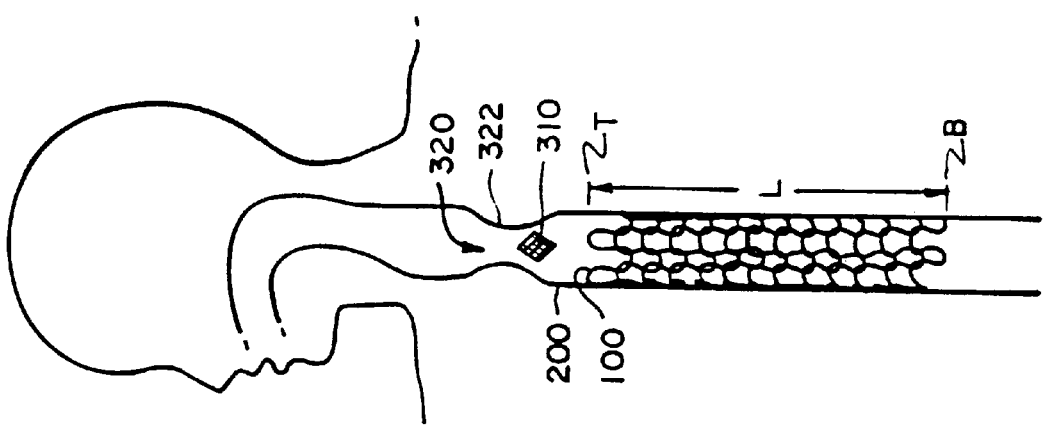
Figure 3E:
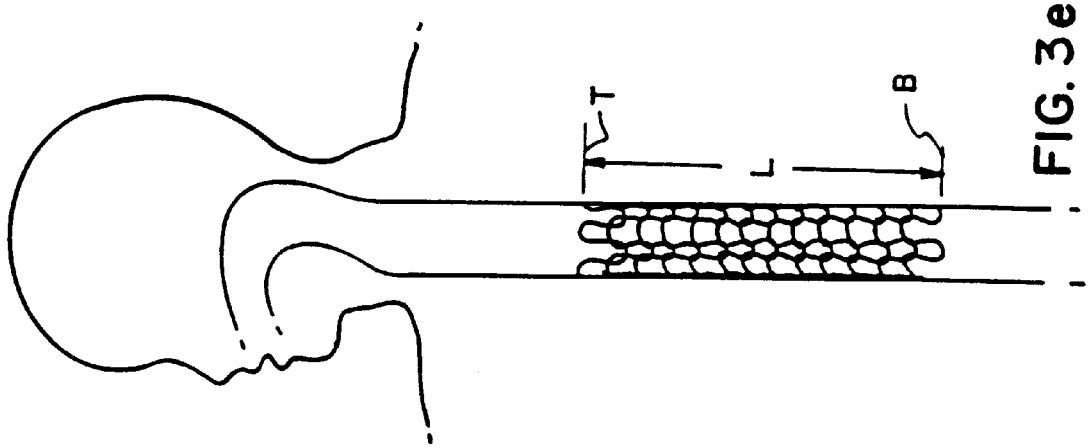
Figure 3D:
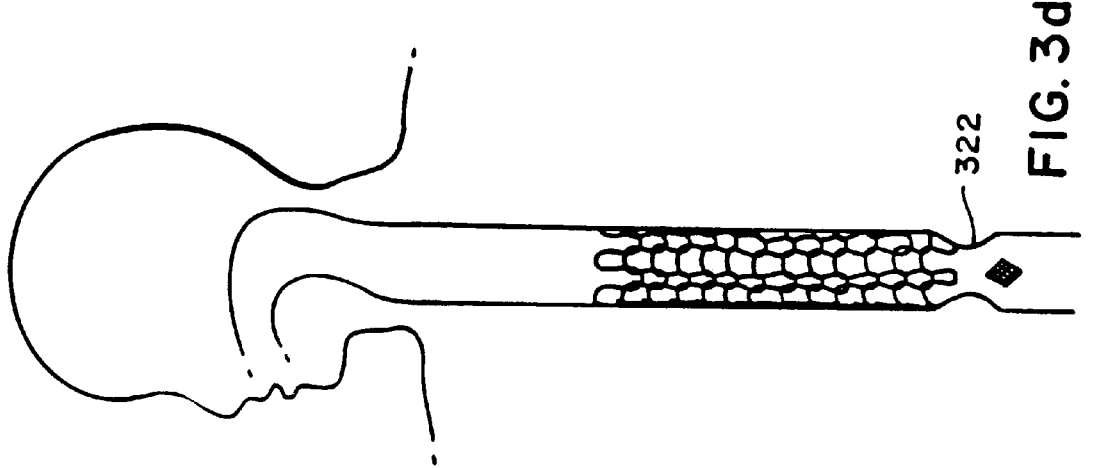
Figure 3C:
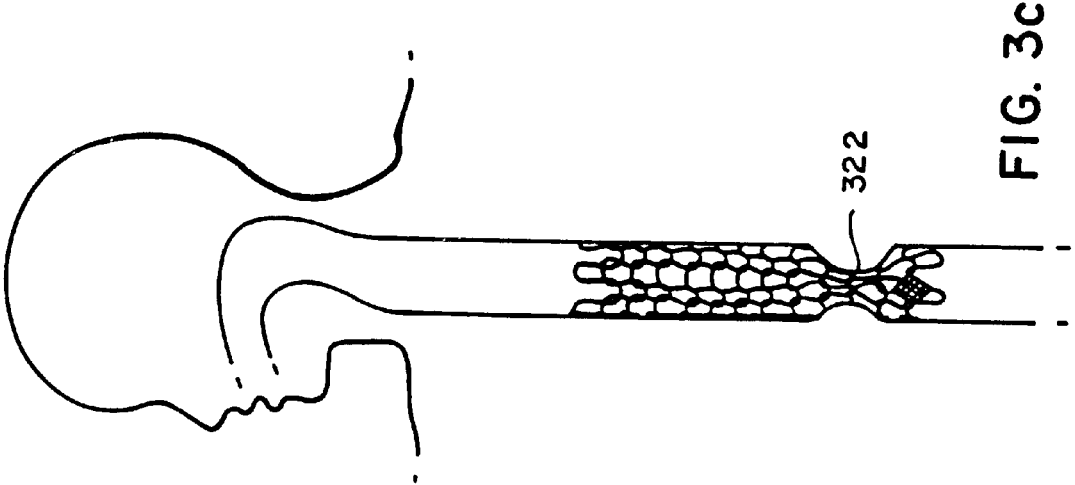

A stent for an organ like the esophagus, according to the invention, not only holds the lumen open but allows the organ to maintain its physiologic motion. Further, the stent adapts to this motion without itself being subject to the peristaltic force—it does not creep toward the stomach with each esophageal contraction, nor does the overall length change. The operation of the elastic knitted stent is illustrated in FIGS. 3 and 3a–3e. A food particle 310 is urged through the lumen 320 by a peristaltic wave 322 that propagates down the esophagus 200. The wave is induced by circumferential contraction of the muscular tissue surrounding the lumen, a consequence of which is radial inward extension of the wall. Before the wave reaches the stented portion, the stent lies between points T and B, with length L between. As the wave reaches point T and the portion of the esophagus reinforced by the stent 100, the stent complies with the radial contraction, as shown in FIGS. 3a–3e. As shown in FIG. 3e, after passage of the peristaltic wave the stent has not migrated from points T and B, and maintains its overall length L. The adjustment and restoration feature allows the stent to maintain its position in the lumen, without migrating axially as might occur with a unitary structure in which stresses in one portion are substantially transmitted to other portions.

Figure 4:
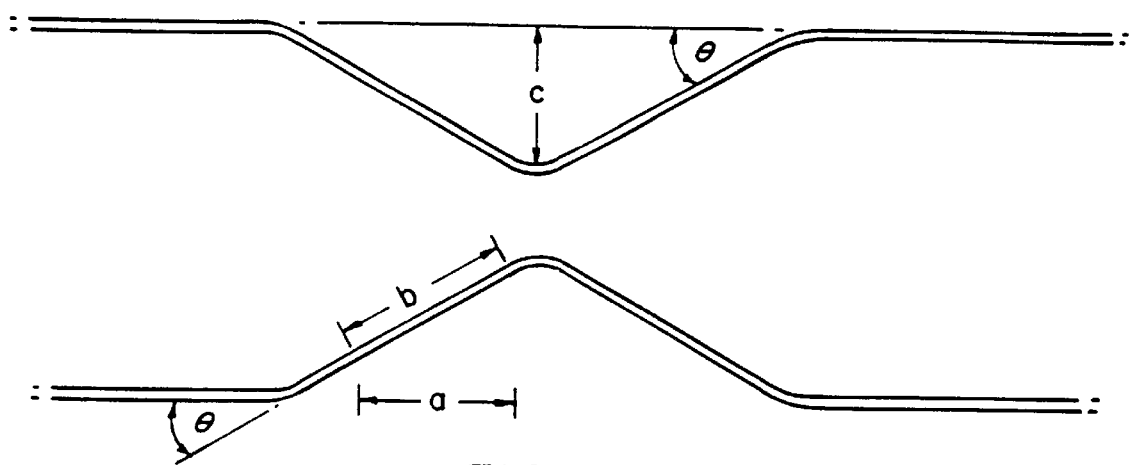
FIG. 4 is a sectional view of a peristaltic organ.
Figure 4A:
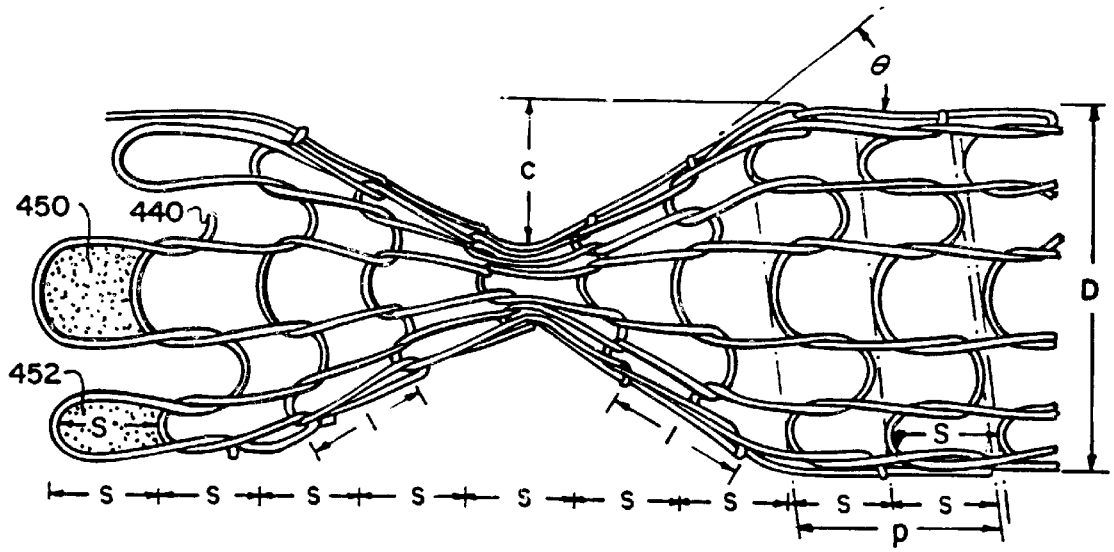

Referring to FIGS. 4 and 4a, the configuration of the knit loops of the stent may be determined based on the degree of radial motion and consequent axial lengthening imposed by the peristaltic motion. Generally, the loop length of the stent in its extended position l can be expressed as:

$$l = \epsilon s \quad (1)$$

where s is the axial length of the portion of the body lumen over which two adjacent loops of the stent extend, and $\epsilon$ is the factor by which the stent must elongate in response to local lengthening of the body lumen wall. It will be seen that the maximum local lengthening will occur over the portion of the wall that lies at the largest angle $\theta$ from the at-rest position. In a worst-case limit, the entire peristaltic wave can be approximated as having a wall at angle $\theta$, thus distending a portion of the lumen that has rest length a to a triangular wave with hypotenuse b. Thus, $$b/a = 1/\cos \theta \quad (2)$$

This ratio, b/a, is the elongation factor by which the loops must lengthen from their relaxed length s to their extended length l to accommodate the lengthening of the lumen wall at the incline of the peristaltic wave. Thus, $$b/a = 1/\cos \theta = l/s = \epsilon \quad (3)$$

For the stent as a whole to maintain point-for-point contact with the wall of the lumen and thus for the stent as a whole to remain stationary along the axis of the lumen, the heads of the loops are allowed to slide locally in the region of peristaltic compression by a distance (l–s)/2.

It will be noted that the stent will accommodate the elongation of the lumen wall if it is capable of local elongation $\epsilon$ equal to $1/\cos \theta$, independent of the amount of deflection c, even in the extreme case where the organ is capable of constricting completely shut—deflection c in FIG. 4a being equal to the radius D/2 of the lumen.

The amount of force exerted by the stent against the lumen wall is chosen to exceed the blood pressure within the capillaries of a typical tumor, and thereby prevent the tumor from further growth into the lumen of the esophagus. The exerted force is determined by the coefficient of elasticity of the filament, by the configuration of the loops and density of the knit (loops per unit of axial length), and by the diameters of the lumen and the stent. For instance, a stent design would exert more force against the lumen wall by choosing a stiffer material for the filament, by knitting the stent with more, smaller loops per unit of length (decreasing s, and reconfiguring the loops to maintain the ratio l/s), or by knitting the stent to a larger rest diameter D. The radial force exerted is bounded at the point where the loops reach the relaxed configuration of FIG. 1b and the stent's diameter reaches diameter D—the forces sum to zero at the contact points 136, and the force exerted on the lumen itself falls to zero. Thus, the diameter D of the stent must be slightly larger than the diameter of the lumen if the stent is to retain its place in the lumen.

Referring again to FIGS. 1, 1a and 1b, a particular embodiment for use as an esophageal stent is knitted of nitinol wire of about 0.15 millimeters in diameter to have a diameter D of about 18 mm, though diameters of 14 mm to 25 mm may be useful. The proximal end 120 is flared to 20 mm, to secure fixation to the esophageal wall. Stents manufactured in overall lengths varying from 5 to 15 cm allow selection of a stent tailored to the patient's needs. The relaxed loop length s is about 0.80–0.85 mm, and the maximum loop length l attained without significantly distorting the loops is about 1.05–1.15 mm. This elongation factor of about 1.4 is close to $\sqrt{2}$, allowing for a maximum angle $\theta$ of about 45°. The peak-to-peak height p of the loops is about 2.2 mm when the loops are in their rest state.

Examples of filament materials include shape memory metals, for example, nitinol, tantalum steel, stainless steel or other elastic metals, or plastics such as polyester, polypropylene, or carbon fiber. The filament may be selected to have a sufficiently high elastic limit to allow the delivery system to rely entirely on this elasticity, rather than, for example, the balloon 820 of FIG. 8e to expand the stent. The filament may be formed of a two-component metal wire system that exhibits desirable physical properties such as enhanced radiopacity along with desirable mechanical properties, such as extreme elasticity. A full discussion of composite medical wires will be found in U.S. application Ser. No. 07/861,253, "Medical Wire" by Kevin R. Heath, incorporated herein by reference. The stent may be knit of two or more filaments.

As shown in FIG. 4a, the stent is knitted of a single filament. This view shows only the front half of the stent. The loops that appear in this view as independent rows in fact are a single spiral-wrapped sequence, much as a common screw has only one ridge from head to tip. In alternate embodiments of the stent, multiple filaments or other knits could be used, so long as the knit structure allows a single row to elongate without forcing the two adjacent rows to shift. The last loop of the wire is cut 440. To prevent the stent from unravelling, the last three loops (two shown, 450 and 452) of the stent are coated in urethane, as shown in FIG. 4b. The coating also covers the sharp ends of the filament.

It will be realized that the stent is applicable to malignant or benign obstructions of many other organs. Stents to treat biliary duct obstructions, for instance when treating liver sclerosis or bleeding, would be about 8 to 10 mm in diameter and 4 to 8 cm in length. Stents for the ureter would be about 6 to 10 mm in diameter and about 2 to 10 cm in length. Urethral stents would be about 10 to 20 mm in diameter and about 2 to 6 cm in length. Stents for the prostatic urethra would be about 10 to 20 mm in diameter and about 2 to 6 cm in length. Colonic stents would be about 10 to 20 mm in diameter and about 4 to 10 cm in length. Stents for hemodialysis shunts would be about 6 to 8 mm in diameter and about 2 to 6 cm in length. Stents for the porta canal would be about 8 to 14 mm in diameter and 4 to 8 cm in length. Stents for the trachea and bronchi would be about 8 mm to 25 mm in diameter and 1 to 8 cm in length. Stents for gastric outlet obstructions would be about 8 to 20 mm in diameter and 1 to 25 cm in length. Peristaltic stents may also be configured for aortic aneurysms or dissections (preferably weaving the filament material with a covering such as dacron), and treatment of superior vena cava syndrome and venous restrictions. The invention is also useful in lumens in which compression is caused by some outside force, for example in blood vessels compressed by muscular contraction, movement of an extremity, or pressure exerted by an object-external to the body.

FIGS. 5, 5a, and 5b represent alternate forms for stents. (Showing the knit loops in these projections would obscure the shape; these figures represent only shapes of the stents.) The stent could be shaped to include, in its free and rest states, a narrowing at a point in its length. This narrowing would accommodate the stent to the anatomy of a natural sphincteric structure, for instance the pylorus or the cardia. A stent so narrowed would enable the organ to close, for instance to prevent reflux. The narrowing could be shaped at one of the ends, for instance for use in the rectum at the anus or in the common duct for a Papilla of Vater.

The narrowing could be shaped conically, as in FIG. 5 for use in sphincter organs. FIG. 5a shows a stent incorporating a flattening, with the circumference in the area of the flattening reduced so that the width remains constant. The latter embodiment could be used in an occlusion with two lips such as the vocal cords. In either case, it may be desireable to form the loops in the region of the constriction so that their free state is similar to one of the compressed configurations, e.g. FIG. 1g, so that the constriction is capable of opening to the rest diameter D.

Figure 5C:
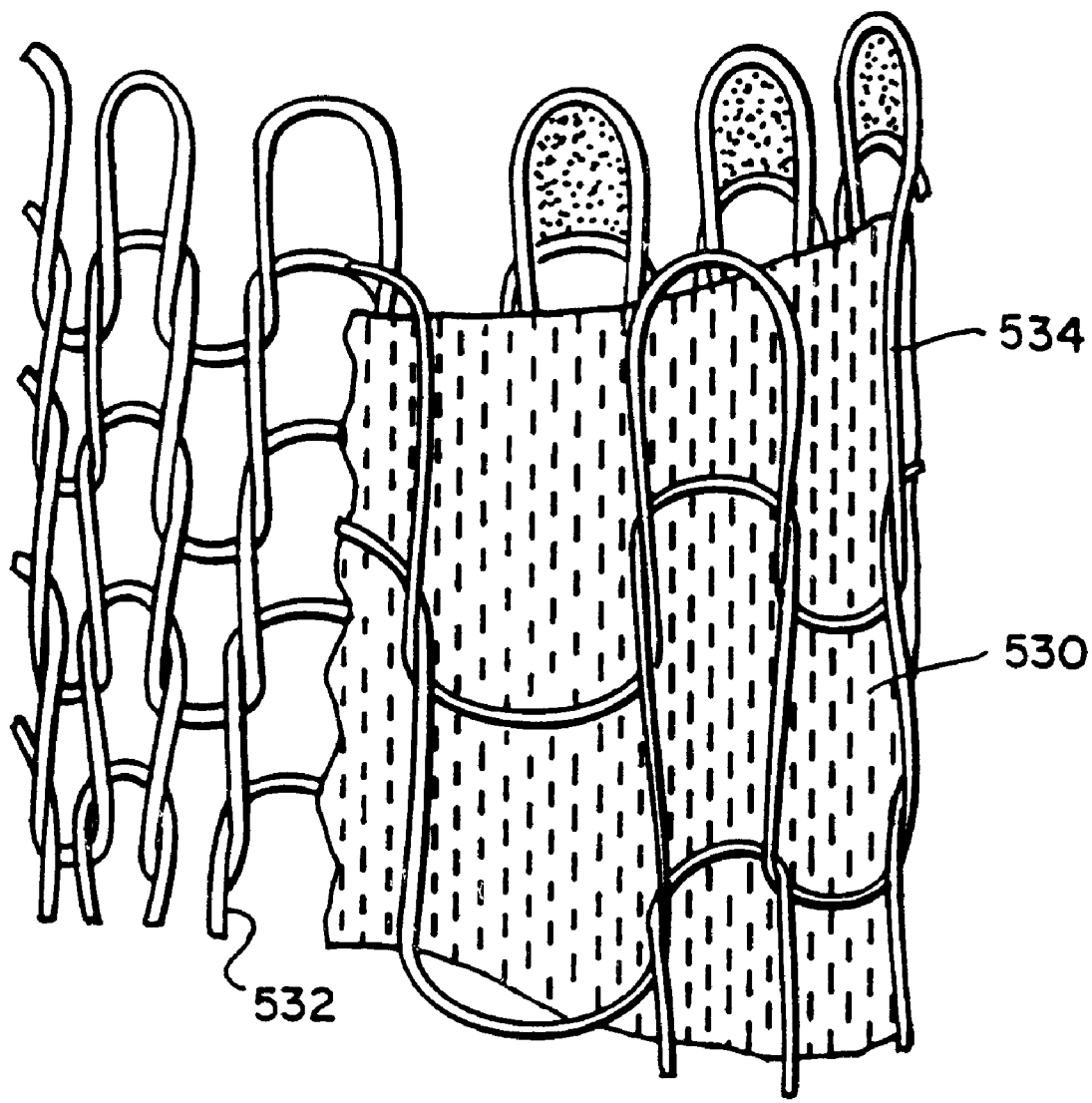
FIG. 5c is a partially broken-away view of an alternate embodiment.

As shown in FIG. 5b, the margins of the narrowing could incorporate a valve to ensure complete closure of the stented organ, as for instance the reinforced lips 520. This valve could be opened and closed either by the muscles normally surrounding the point of constriction or by a manually-operated control extended to outside the body. This would allow the use of the stent, for instance, across the aortic valve or as a replacement for the urinary sphincter. It may be desireable to reinforce the point of the constriction, e.g., with a stiff wire, especially in conjunction with the flattened constriction of FIG. 5a. It may also be desireable to provide a valved stent with a watertight membrane, similar in form to that discussed below and shown in FIG. 5c.

The stent can be made to exert varying force along its length, for instance by varying the gauge of the wire or the density of the knit. In the narrowed stents discussed above, it may be desireable to make the stent particularly flexible in the region of the narrowing.

Some tumors are so invasive that the stent is quickly ingrown by the tumor. As shown in FIG. 5c, the stent may be manufactured with an elastic semi-permeable membrane 530 of porosity less than 50 microns and of very low modulus of elasticity, sandwiched between two knit layers. The membrane may advantageously be of expanded polytetrafluoroethylene (teflon) or latex. The inner layer 532 is essentially identical to the single-layer stent, providing most of the elastic force against the lumen. The outer knit layer 534, which acts to retain the membrane, is typically constructed of thinner wire, for instance 0.07 mm diameter, or a less-resilient material such as polypropylene or polyethylene. The outer knit layer is slightly shorter in length than the inner layer.

Figure 6:
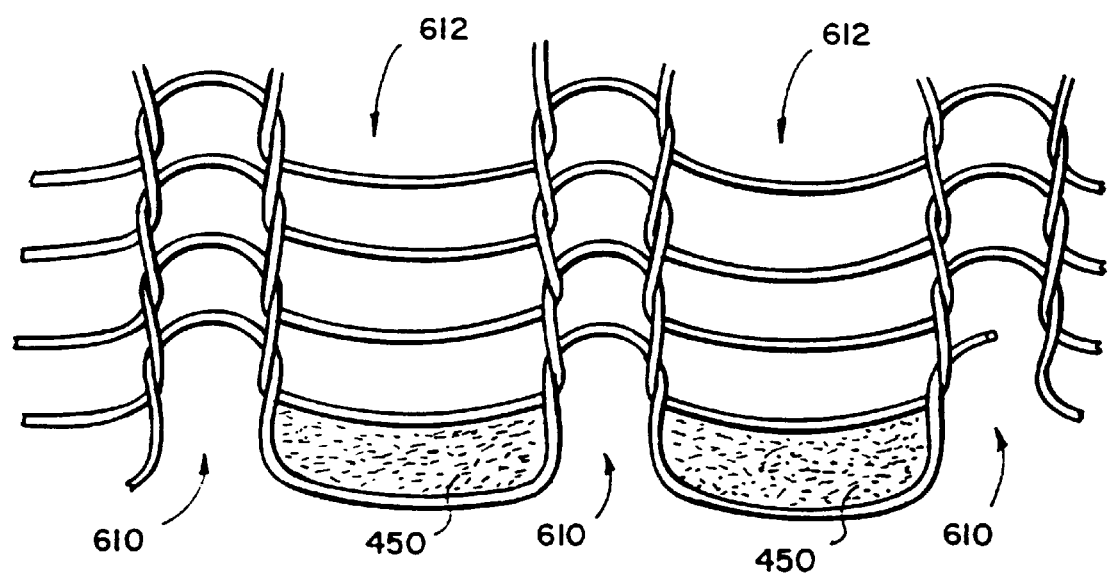

The stent is knit on a conventional knitting machine, very similar to that used to knit stockings. During the knitting process, the wire is deformed past its elastic limit. Referring to FIG. 6, on some knitting machines, or for stents of some diameters, it may be convenient to produce a knit with the "up loops" 610 of a different shape than the "down loops" 612. In some applications, for instance the aorta, it is important that the loops be uniform so that the stent exerts uniform pressure along the-lumen wall. During the knitting process, the wire will be under tension, and thus the loops will be in a tight configuration, similar to FIG. 1e, or possibly to FIG. 1f or 1h depending on the geometry and setup parameters of the knitting machine itself.

Figure 6A:
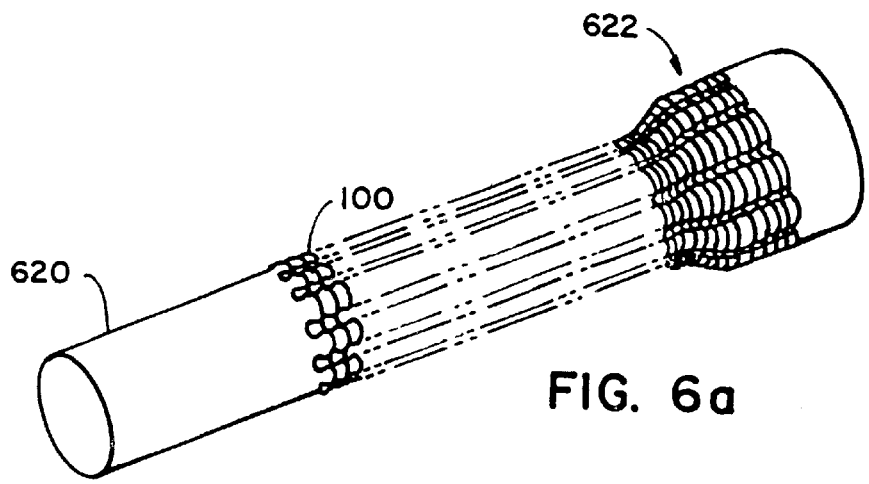

The knitting machine produces a long "rope" of knit loops. The rope is cut into lengths somewhat longer than the final length of the stent. The extra length allows for the shortening of the stent that will occur as the loops are shortened from the elongated state in which they emerge from the knitting machine to the rest state of FIG. 1b, and allows for some trimming. As shown in FIG. 6a, after knitting, the stent is mounted on a mandrel 620 for annealing, to relieve the strains induced by the plastic deformation of knitting and to produce greater elasticity in the wire. The mandrel is in the free shape of the stent, 18 mm in diameter with a flare 622 to 20 mm at one end. To achieve the constricted embodiments of FIGS. 5 and 5a, the mandrel would have a constriction formed in it, and an external restraint would be applied to the stent so that the annealed shape would be as shown in those figures. As the stent is loaded onto the mandrel, the operator shortens the overall length so that the loops assume the relaxed, shortened state of FIG. 1b. The stent is annealed at approximately 450° C. for about 15 minutes.

After annealing, the stent is cut to its final length, and the three loops at each end of the stent each receive a drop of urethane (450 of FIG. 4a or FIG. 6) to prevent unravelling.

Figure 6B:
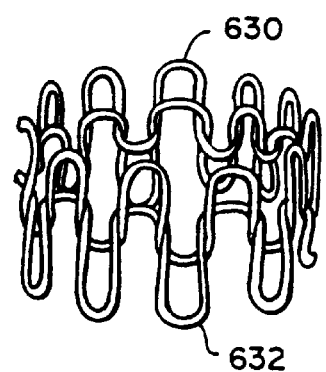

Alternately, the stent may be knit of interlocking preformed sinusoidal rings, two of which 630, 632 are shown in FIG. 6b.

Figure 7:
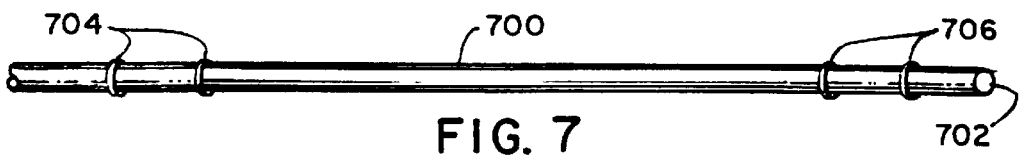
Figure 7A:
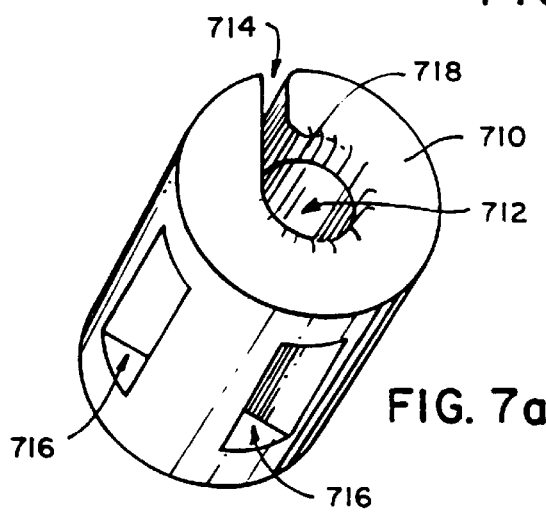

The stent itself is packaged into a delivery catheter as shown in FIGS. 7 and 7a–7u. The center of the delivery catheter is a carrier tube 700, shown in FIG. 7. The carrier is a flexible tube of Pebax, a polyether/polyamide-12 resin from Atochimie with desireable flexibility/rigidity characteristics, 2.5 mm in diameter and approximately 80 cm long. The carrier has several radiopaque O-rings 704,706 mounted along the most-distal 20 cm. The preferred radiopaque material is tantalum.

Figure 7B:
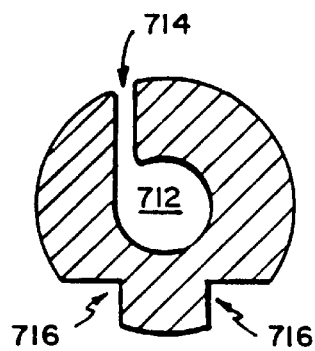
Figure 7C:
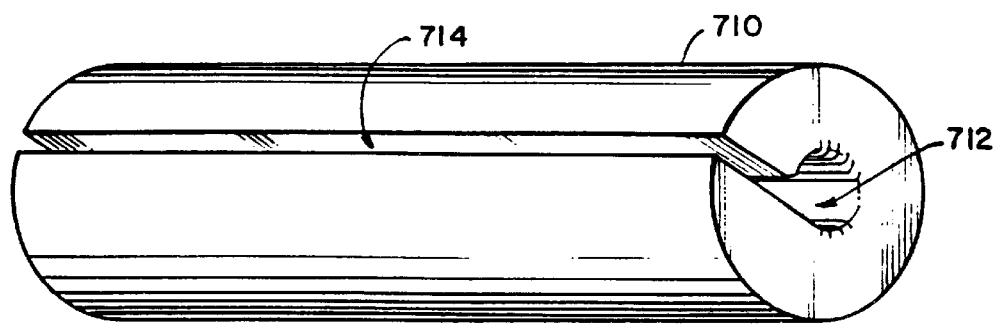
Figure 7D:
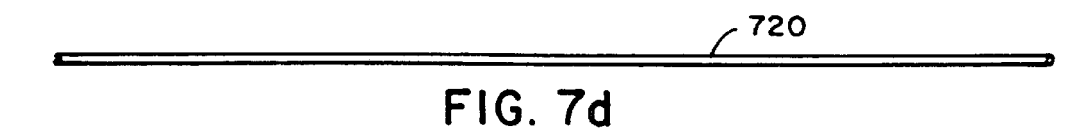
Figure 7E:
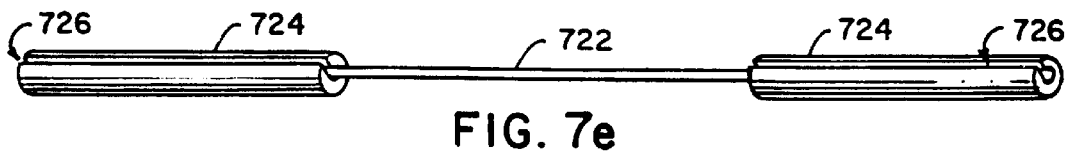
Figure 7F:

The preferred process of mounting the stent on the carrier tube 700 uses several tools: a confining block, two mandrels, and a pusher. The confining block 710, shown in FIGS. 7a–c, is cylindrical, somewhat longer than the stent itself at about 20 cm, and formed of a rigid plastic with low friction characteristics, preferably delrin or nylon. The block has a drilled bore 712 of 8 mm diameter, with a 1 mm-wide slot 714 cut from the top of the outside of the block and meeting the inner bore 712 at a tangent. The slot and bore may have a guideway 718 formed, to make the following steps easier. The block may also have flats 716 milled in the bottom so that the block may be mounted in a vise. A first mandrel 720, shown in FIG. 7d, is a simple rod approximately 30 cm long and about 3 mm in diameter. A second mandrel 722, shown in FIG. 7e, has a shaft of about 3 mm diameter and length longer than the confining block, two handles 724, each about 10 mm in diameter, with center bores that friction fit on the ends of the mandrel shaft, and slots 726 of width to accommodate the carrier tube. Both mandrels have rounded ends so that they will not catch on the loops of the stent. A third tool is a pusher 728, shown in FIG. 7f, with a shaft 729 of slightly less than 8 mm diameter and a bore 730 somewhat larger than the outer diameter of the carrier 700. The bore may either be the full length of the pusher, or as shown in FIG. 7f, may have a breech hole 732. A fourth tool, which will be seen in FIG. 7q, is a soft copper wire with a silicone sheath 760 (silastic) over it. The sheathed wire is about 50 cm long, and the sheath is about 1–2 mm in diameter.

Figure 7G:
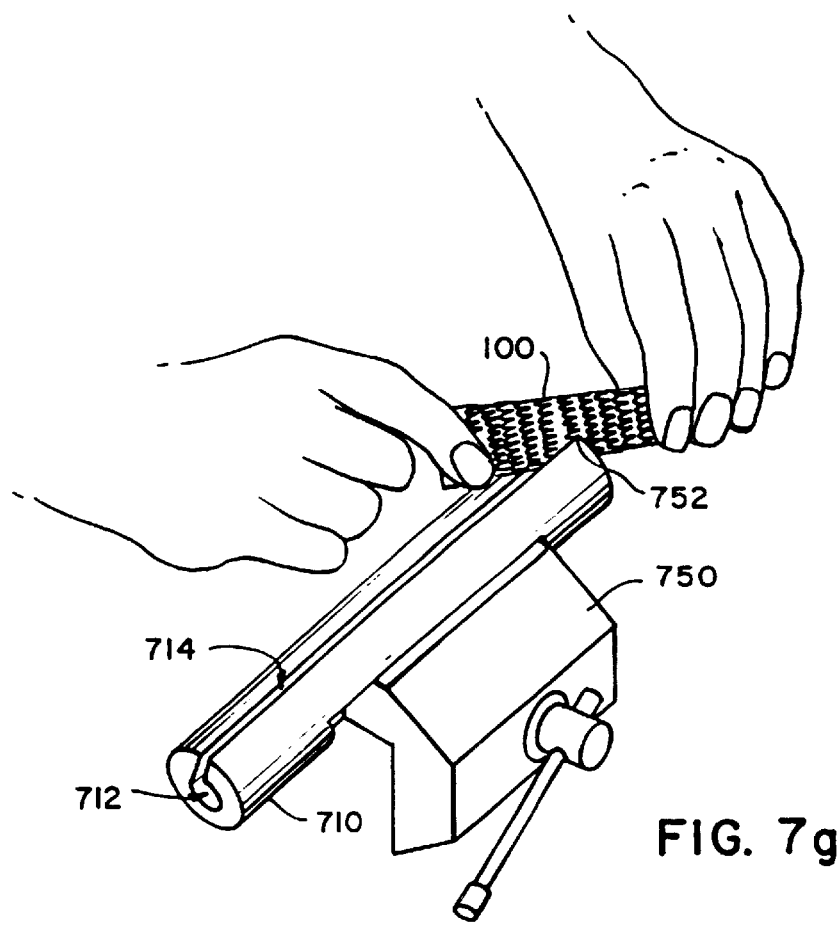
Figure 7H:
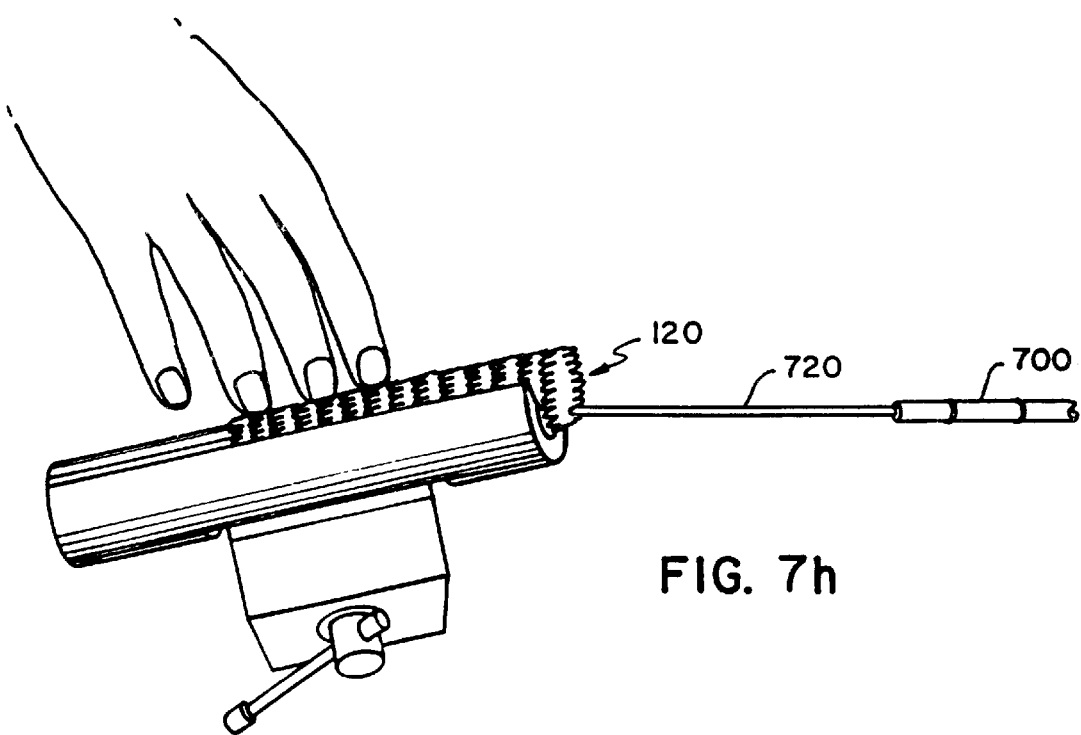
Figure 7M:
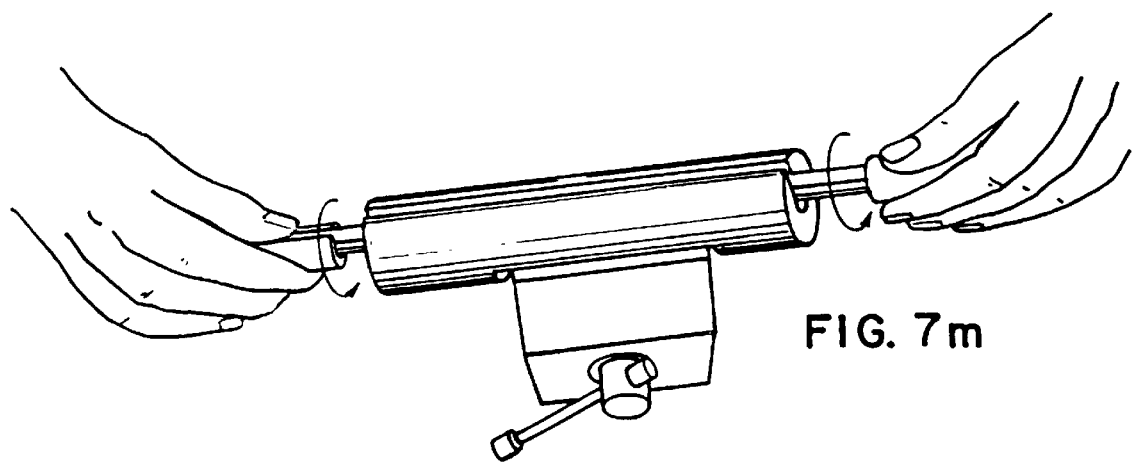
Figure 7N:
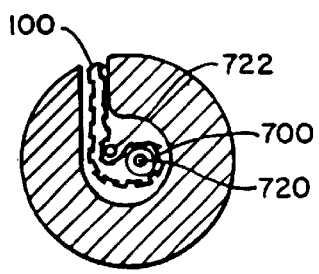
Figure 7O:
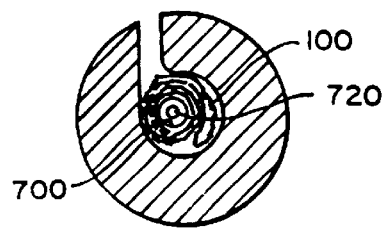

Referring to FIG. 7g, the confining block 710 is securely mounted, as in a vise 750. An operator squeezes a stent 100 flat and works it into the slot 714 preferably starting at a corner 752, and bottoms it in the bore 712. Referring to FIG. 7h, the stent is positioned in the confining block so that the proximal end 120 of the stent extends from the end of the confining block. The first mandrel 720 is inserted into the distal end of the carrier 700, and then the mandrel and carrier tube are passed through the center of the stent. The operator slides the stent to the center of the confining block, as shown in FIG. 7i. Referring to FIG. 7j, the stent is slid back so that the flared proximal end again extends from the end of the confining block. One handle of the second mandrel is removed, and the shaft 722 of the second mandrel inserted through the bore of the confining block but outside the stent. Referring to FIG. 7k, the first mandrel 720 lies inside the carrier tube 700, which in turn lies inside the stent 100. The lower portion of the stent and the second mandrel 722 lie inside the bore 712 of the confining block. Referring to FIG. 7l, the stent is slid back to the center of the confining block. The several slides forward and back equalize the distribution of the knit loops evenly over the length of the stent. The second handle of the second mandrel is affixed to the shaft of the second mandrel, and the slots 726 of the handles engaged with the carrier tube 700 and/or first mandrel 720. The operator can center the O-rings 704,706 within the stent so that the carrier will be axially positioned roughly correctly within the stent. Referring to FIG. 7m, the operator twists the handles, revolving the two mandrels about each other and winding the stent about the two mandrels. FIG. 7n shows the configuration of the stent and the two mandrels after about half a revolution. The operator continues winding until the stent is completely rolled on itself in the bore of the confining block. The operator removes a handle from the second mandrel and removes the second mandrel from the confining block. The stent is held in the wound conformation by the confining block, as shown in FIG. 7o.

Figure 7P:
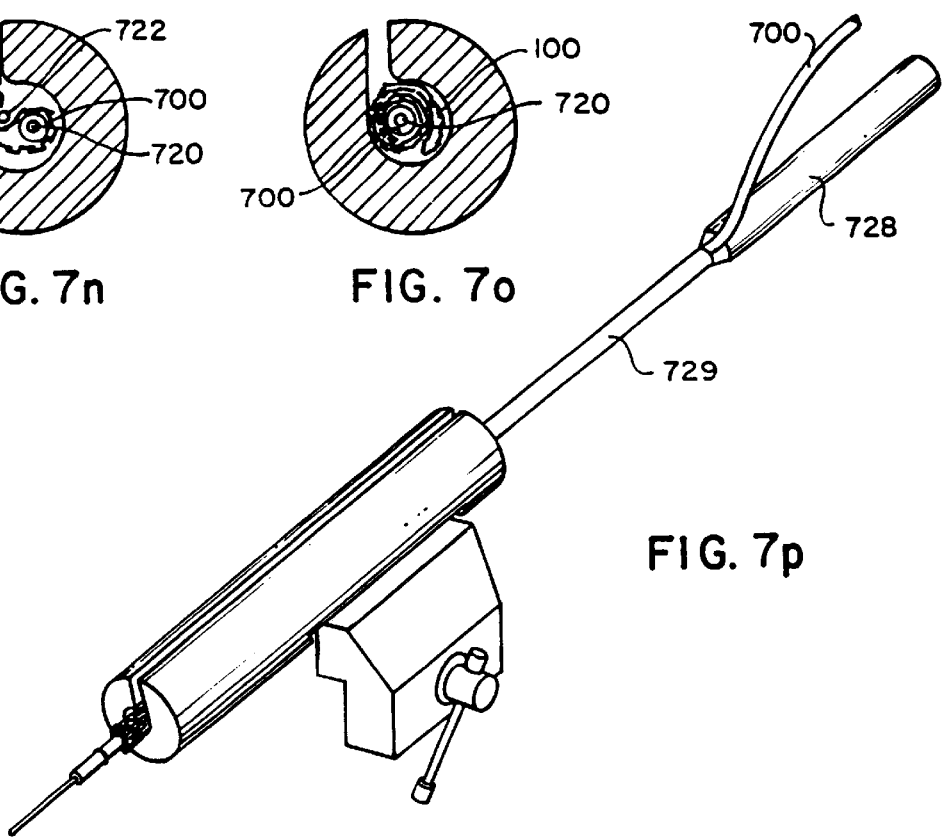
Figure 7Q:
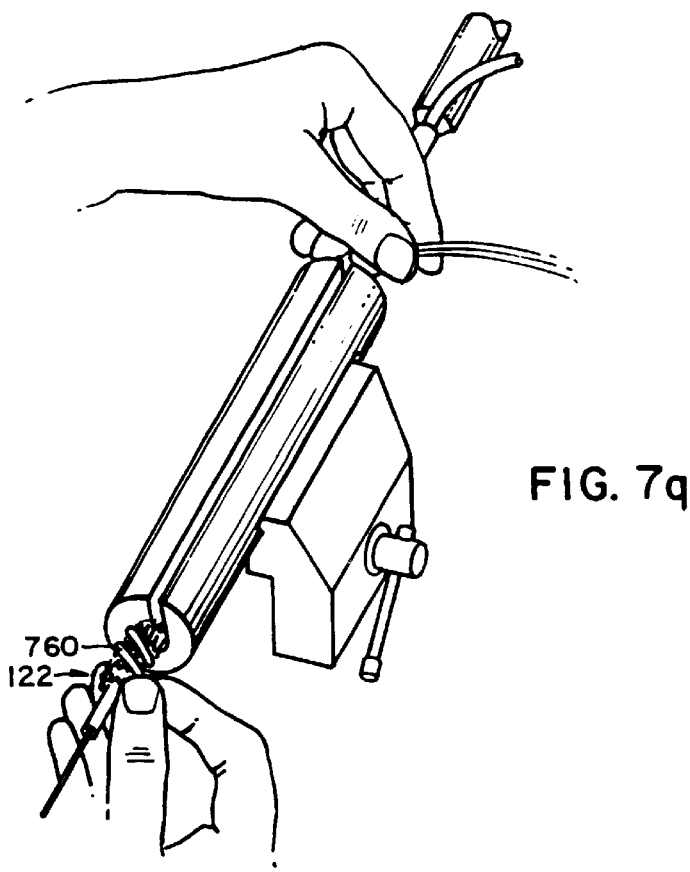

Referring to FIG. 7p, the operator threads the pusher 728 over the proximal end of the carrier, with the shaft 729 distal. The pusher will be used to slowly push the stent out of the bore of the confining block.

Figure 7R:
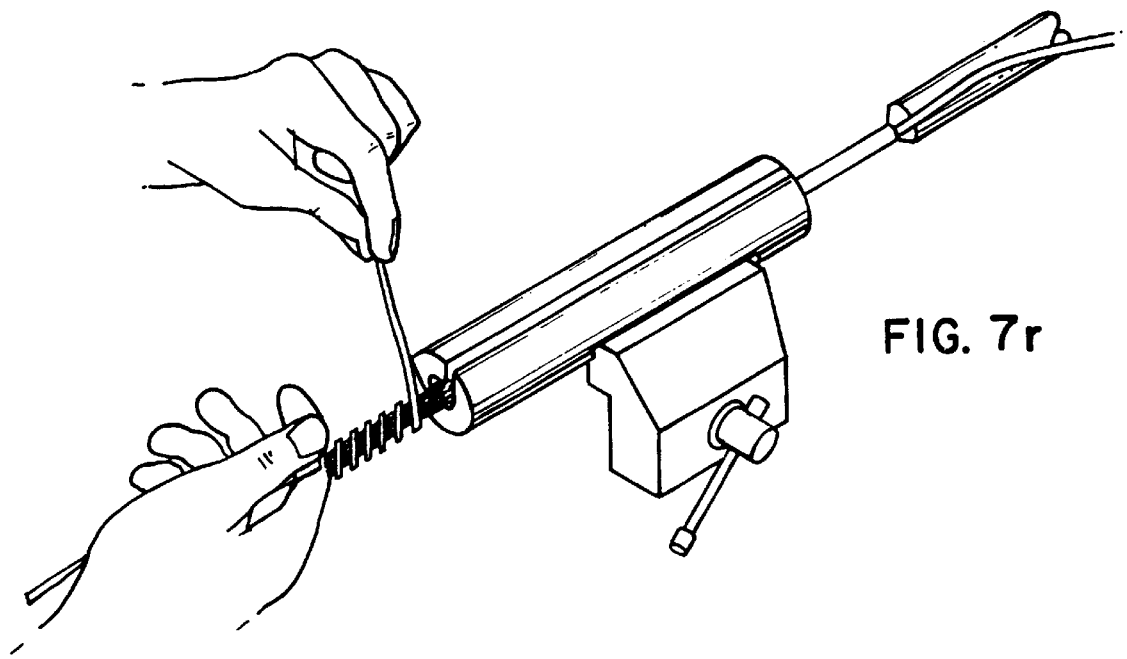

Referring to FIG. 7q, using the pusher the stent is pushed out of the confining block by about 1 cm. The operator makes any final adjustments required to center the radiopaque O-rings within the stent. The operator wraps several turns of the copper wire and silicone sheath 760 around the exposed distal end 122 of the stent, with about a 1 mm gap between turns, and lays the bight of the sheathed wire into the slot of the confining block. Referring to FIG. 7r, the operator gradually feeds the stent out of the confining block using the pusher, and wraps the sheathed wire around the stent to keep it confined to a diameter of about 8 mm. The operator maintains a roughly uniform 1 mm spacing between wraps.

After the stent is fully bound in the copper wire 760, the pusher is removed back over the proximal end of the carrier tube and the carrier tube is pulled out of the bore of the confining block, the stent and silastic/copper wrap is dipped in U.S.P. grade dissolving gelatin, and the gelatin is allowed to set. The copper wire can then be unwrapped; the silicone sheath acts as a release surface so that the gelatin peels off the wire and remains set on the stent in a 1 mm-wide "threaded" strip, 770 in FIG. 7s, confining the stent.

Referring to FIGS. 7t and 7u, the stent delivery system catheter 799 is completed by affixing a nose piece 772 onto the distal end of the carrier 700, and surrounding the entire assembly in a cylindrical sheath 774. Both the carrier and sheath are essentially rigid in the axial direction, so that they can be used to push or pull the catheter to position it, and so that handles 782 and 784 can be squeezed together to retract the sheath from over the stent. Also shown in FIG. 7t are the radiopaque markers 704,706 and in FIG. 7u graduation markings 778 on the sheath, both of which will be used during implantation to guide positioning. The inner pair of the markers indicate the length the stent will assume at its 18 mm fully-expanded diameter, and the outer pair indicate the length of the stent when compressed to 8 mm diameter. A guidewire 778 will be threaded through the center bore 776 of the carrier during implantation.

The process of implanting the stent is illustrated in FIGS. 8 and 8a–8e. Referring to FIG. 8, using an endoscope 810, the proximal margin 812 of a stricture 814 is identified. The guidewire 778 is advanced across and beyond the stricture. In FIG. 8a, an 8 cm-long balloon 820 is advanced over the guidewire and inflated to 12 mm diameter, dilating the stricture to 12 mm. After examining the stricture endoscopically and fluoroscopically, a gelatin-encased stent 4–6 cm longer than the stricture is chosen. The delivery system 799 is passed over the guidewire and advanced until the distal inner radiopaque marker 704 is 2–3 cm below the distal margin 832 of the stricture.

Referring to FIG. 8c, The outer sheath is retracted by squeezing together handles 782 and 784 (see FIG. 7u), and the stent begins to deploy. The gelatin will immediately begin to dissolve, allowing the stent to expand under its own elastic restoring force. The material of the stent filament, nitinol, is chosen so that even the fairly severe deformation required to compact the stent into the delivery system does not exceed the elastic limit. Referring to FIG. 8d, after the proximal 120 and distal ends 122 of the stent have expanded and firmly attached to the esophageal wall, the catheter 799 can be removed. Referring to FIG. 8e, depending on the patient, a 12 mm-diameter balloon 820 may be inflated within the stent to ensure that the occlusion is opened to the desired patency, to affix the stent firmly to the esophageal wall, and to ensure adequate esophageal lumen size for endoscopic examination. Peristaltic contractions of the esophagus will allow the stent to "settle" into its most-relaxed configuration.

Figure 9:
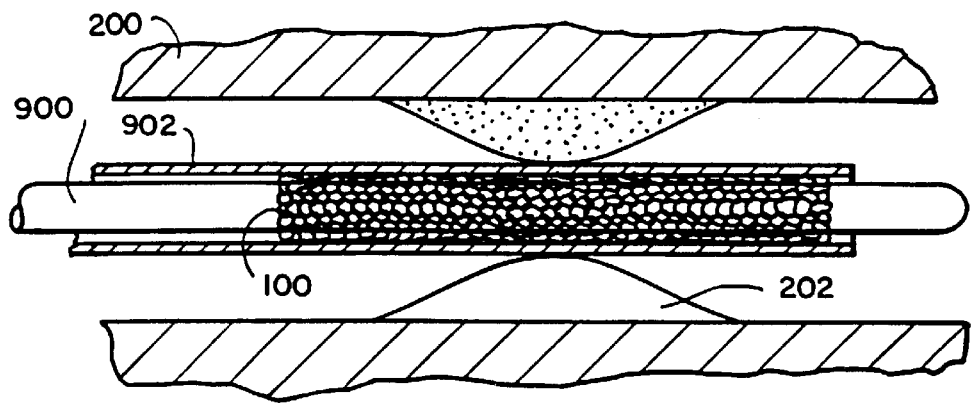
FIGS. 9, 9a, and 9b are a time sequence of cutaway views of an alternate delivery method.
Figure 9A:
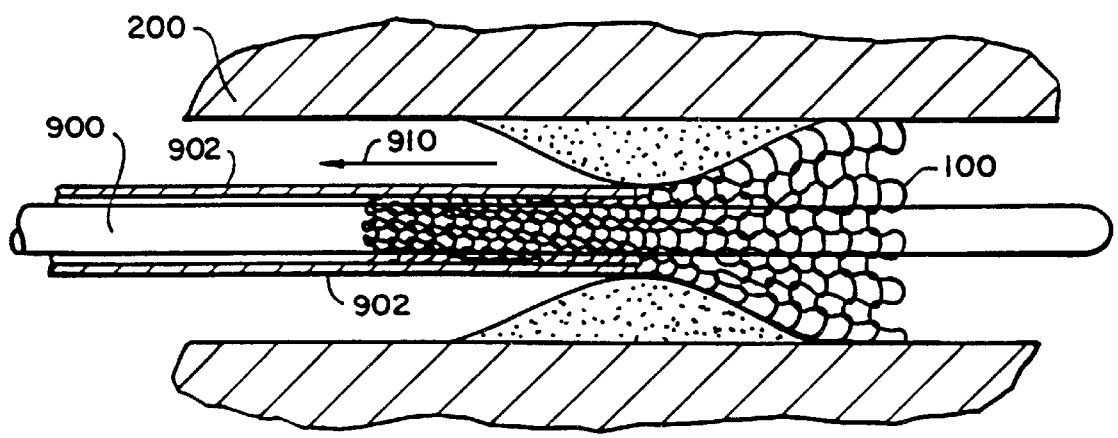
Figure 9B:
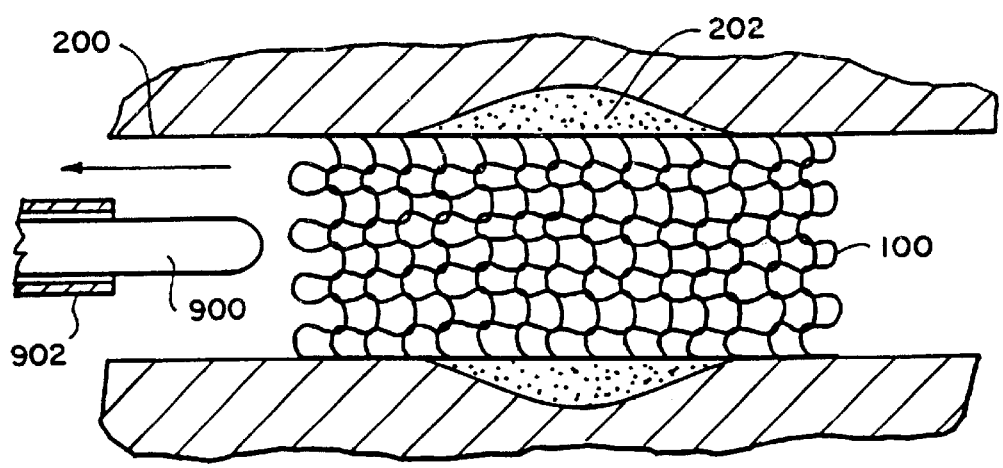

Referring to FIG. 9, in another delivery system, the stent 100 is formed of an elastic filament material that is selected so compaction produces internal restoring forces that allow the stent to return to its rest diameter after the compacting restraint is removed. The stent may be compressed onto a catheter 900 that includes a sleeve 902; the sleeve holds the stent in a relatively compacted state. The compaction is typically achieved by rolling the stent upon itself using two mandrels, as in FIGS. 7g–7o. In other cases, the stent may be positioned coaxially over the catheter. The catheter is positioned within the lumen at the region of the tumor 202. In FIG. 9a, the sleeve is removed from about the stent, for example, by withdrawing axially in the direction of arrow 910, thus allowing the stent 100 to radially expand by release of its internal restoring force. As shown in FIG. 9b, the axial force exerted by the stent is sufficient to dilate the lumen 200 by pushing the tumor growth 202 outward, or in some cases to compress the occlusion against the lumen wall. The catheter can then be removed.

Other embodiments are within the following claims.

What is claimed is:

1. A method for manufacturing a system for delivering a resilient tubular device into a body by reducing said tubular device from a rest diameter to a substantially reduced diameter, the method comprising the steps of:

providing a confining block having a bore at least as large as said reduced diameter and a slot in a side of said confining block, said slot having an end at said bore;

pinching a flat line in said tubular device;

inserting the pinched portion of said tubular device into said confining block, the pinched line of said tubular device lying in said slot and a contiguous portion of said tubular device lying in said bore;

inserting a first mandrel into the portion of said tubular device lying inside said bore;

inserting a second mandrel into said bore but outside said tubular device;

revolving said mandrels relatively about each other to roll said tubular device on itself until said tubular device is entirely rolled and has said reduced diameter within said bore; and removing said tubular device from said bore while restraining said tubular device in its reduced diameter condition.

2. The method of claim 1 wherein said removing step comprises:

slowly pushing said tubular device from an end of said bore and restraining said tubular device as it emerges.

3. The method of claim 2 wherein said restraining comprises wrapping a wire around said tubular device.

4. The method of claim 1 wherein said slot is tangent to said bore of said confining block.

5. The method of claim 1 wherein said tubular device comprises a stent knit of an elastic filament.

6. The method of claim 5 wherein said first mandrel comprises an elongated delivery carrier for said stent.

* * * * *